(12) United States Patent
Lipshitz et al.

(10) Patent No.: US 7,008,448 B2
(45) Date of Patent: Mar. 7, 2006

(54) INTRAOCULAR IMPLANT FOR RETINAL DISEASES

(75) Inventors: Issac Lipshitz, Heartleaf Paducah (IL); Yariv Lipshitz, Raanana (IL)

(73) Assignee: Isaac Lipshitz, Heartleaf Paducah (IL)

( * ) Notice: Subject to any disclaimer, the term of this patent is extended or adjusted under 35 U.S.C. 154(b) by 0 days.

(21) Appl. No.: 10/844,327

(22) Filed: May 13, 2004

(65) Prior Publication Data

US 2004/0236421 A1 Nov. 25, 2004

Related U.S. Application Data

(63) Continuation-in-part of application No. 10/316,006, filed on Dec. 11, 2002, now Pat. No. 6,913,620, which is a continuation-in-part of application No. 10/108,458, filed on Mar. 29, 2002, now Pat. No. 6,902,577.

(60) Provisional application No. 60/470,489, filed on May 15, 2003.

(51) Int. Cl.
*A61F 2/16* (2006.01)

(52) U.S. Cl. .................................... 623/6.31; 623/6.32

(58) Field of Classification Search ............... 623/6.17, 623/6.32–6.36
See application file for complete search history.

(56) References Cited

U.S. PATENT DOCUMENTS

| 4,994,082 A | * | 2/1991 | Richards et al. | ........... 623/6.32 |
| 5,578,080 A | * | 11/1996 | McDonald | ................. 623/6.17 |
| 6,264,693 B1 | * | 7/2001 | Ross | ........................ 623/6.17 |

* cited by examiner

*Primary Examiner*—Corrine McDermott
*Assistant Examiner*—Hieu Phan
(74) *Attorney, Agent, or Firm*—Mark M. Friedman

(57) ABSTRACT

An intraocular implant for implantation into the interior of a human eye, the eye having a retina, the implant comprising a body member and an optical arrangement. The body member has an anterior surface, a posterior surface and optical properties. The optical arrangement is configured for forming a first image on the retina. The first image is an image of at least part of the central visual field. The body member and/or the optical arrangement are configured for forming a second image on the retina. The second image is an image of at least part of the peripheral visual field.

25 Claims, 38 Drawing Sheets

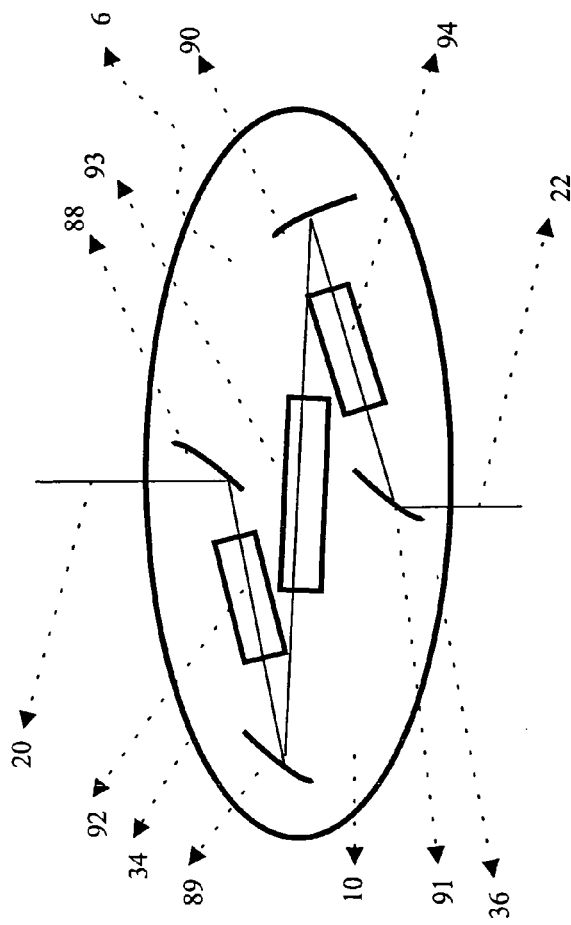
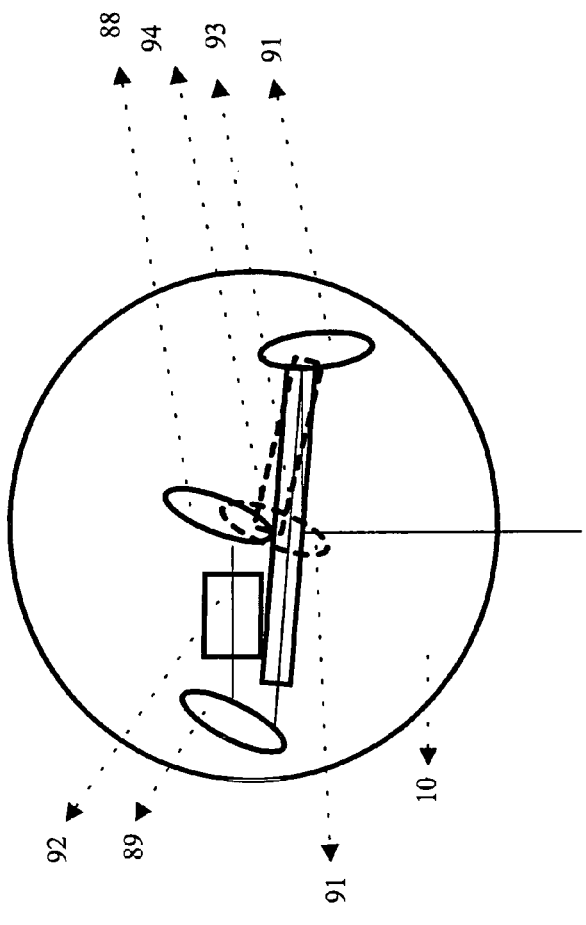
Figure 21a
Figure 21b

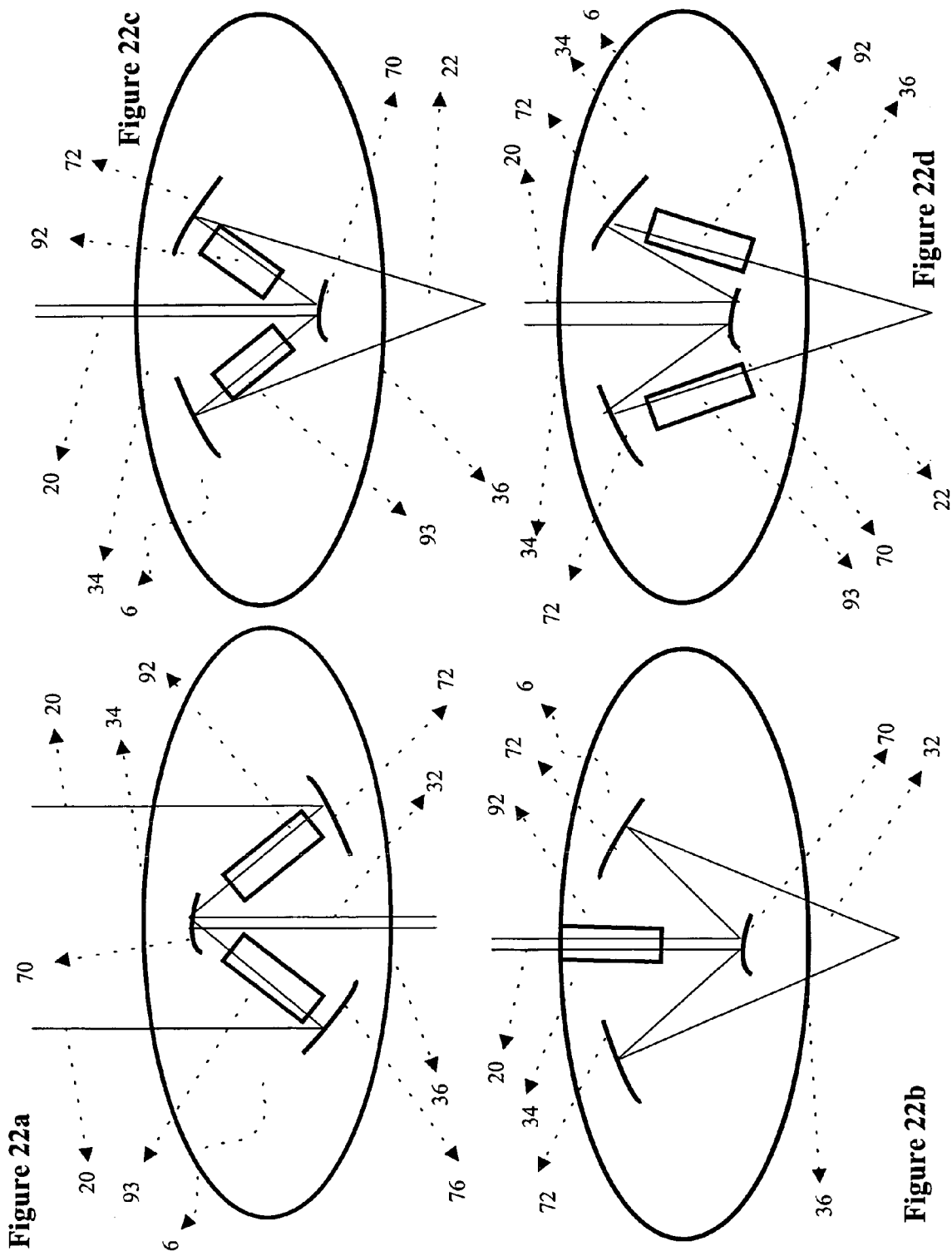

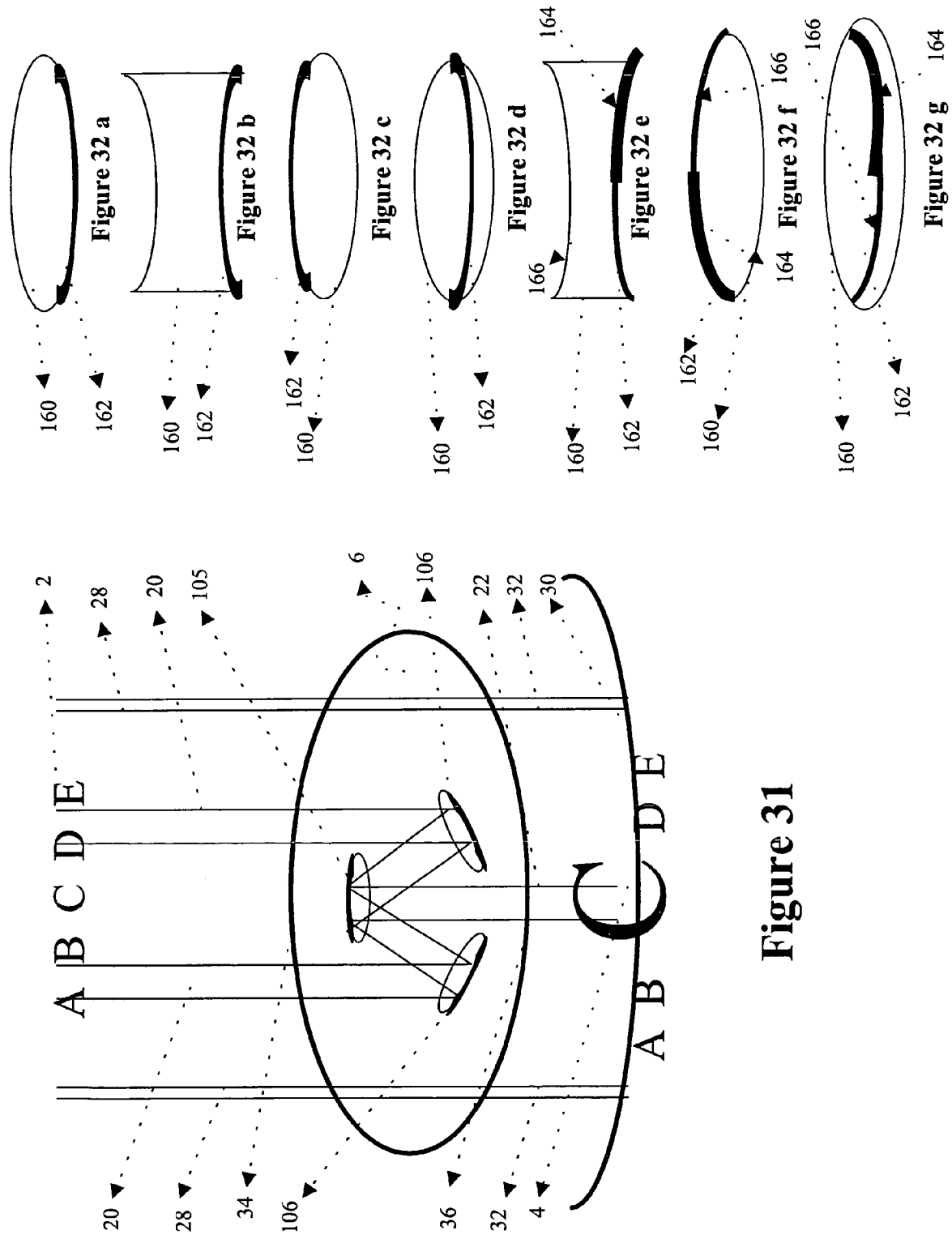

INTRAOCULAR IMPLANT FOR RETINAL DISEASES

This application claims priority from U.S. Provisional Application Ser. No. 60/470,489 filed May 15, 2003 and U.S. application Ser. No. 10/316,006 filed Dec. 11, 2002 now U.S. Pat. No. 6,913,620 which in turn claims priority from U.S. application Ser. No. 10/108,458 filed Mar., 29, 2002 now U.S. Pat. No. 6,902,577.

FIELD AND BACKGROUND OF THE INVENTION

The present invention relates to intraocular implants for implantation in the human eye and, in particular, it concerns intraocular implants having a combination of optical elements such as lenses, lenses coated as mirrors, mirror, magnifying element, prisms of various forms and semi transparent mirrors.

By way of introduction, there are many ocular diseases where the patient's vision can be improved using optical implants into the eye. Macular degeneration (hereinafter, "AMD") is one if these disorders. Eyes suffering from AMD are damaged in the center of the visual field and the patients, usually the older population, maintain their peripheral vision, but lose their central vision. These patients are not blind. They can navigate in their surroundings and they do not stumble over chairs or other furniture. However, when they need their central accurate vision they see a black central spot and they are therefore unable to read, write, drive, work on a computer, recognize faces. They even have difficulty eating. At the final stage of this disease the patient becomes legally blind. Although AMD is the most common central retinal degeneration disease (about 25–30% of the population over 75) there are many other diseases that cause damage to the central or peripheral visual field, for example, but not limited to, diabetic retinopathy, ocular vascular accident, retinal dystrophies (such as Retinitis Pigmentosa).

In a normal eye, the central vision is used for focused vision, for example, for reading. The extraocular muscles move the globe of the eye so that the image of an object being viewed always appears on the point of central vision that occupies only a small fraction, less than 10%, of the retina, known as the macula. The bulk of the retina is used for peripheral vision, which serves primarily for orientation in space. The visual acuity of this bulk area is not as sharp as the macula. Thus, central vision provides a relatively small field of view with very high resolution for perception of details, while peripheral vision provides a wide field of view with relatively low resolution, providing sufficient information for navigation and detection of targets of interest.

Of relevance to the present invention is U.S. Pat. No. 4,759,761 to Portnoy, which teaches a catadioptric intraocular lens containing interior mirrored surfaces forming a folded telescope. The lens of Portnoy patent suffers from many limitations similar to those of an Intra-Ocular Telescope (hereinafter "IMT"). IMT devices are taught by U.S. Pat. Nos. 5,354,335 and 5,392,202 to Lipshitz, et al. A shortcoming of the lens of Portnoy is that it does not preserve nor permit peripheral vision because the mirrors cover the entire pupillary aperture. Therefore, the device of Portnoy produces a limited magnified central visual field only. Furthermore, the device of Portnoy is not structured for use with other diseases, such as diabetic maculopathy, retinitis pigmentosa or advanced glaucoma, as the mirrors cover the entire pupillary aperture, the natural peripheral visual field is obscured and it is therefore almost impossible to examine the retina or treat it. Also the IMT devices as well as the device of Portnoy, (which was never built or used in clinical practice) can only be implanted into one eye as one eye needs to be used for central vision and the other eye for peripheral vision as the implant does not allow both visions in one eye. This leads to several limitations including: anisoconia (difference in image size between the eyes), a difference in the angular velocity of moving objects between the eyes and the need for prolonged rehabilitation due to the two eyes having different visual performance (one eye for a magnified central visual field and the other for the normal peripheral visual field). Furthermore, if in the future, one eye severely deteriorates the patient cannot function with only one eye as he can either use the one eye for central vision or peripheral vision, but not both.

Copending U.S. application Ser. Nos. 10/108,458 and 10/316,066 to Lipshitz, disclose an optical implant that not only magnifies the central visual field but also preserves at least some of the peripheral vision, thus, the patient who has this device implanted into his eyes not only sees a magnified image in the central visual field but also has at least some peripheral vision in the same eye. According to these copending patent applications, the device can be implanted in both eyes thus eliminating many problems that are created by the IMT and the Catadioptic Lens taught by Portnoy There is therefore a need for an intraocular implant for treatment of defects in central vision, including AMD and other disorders of the macula, as well as increasing the central visual field while preserving at least some peripheral vision, and other disorders of vision, such as regular cataracts, while preserving the natural unchanged peripheral visual field, devoid of the above limitations.

Additionally, it would be desirable to have a device that permits a full normally sized visual field with a magnified central image for seeing precise objects such as for reading while preserving peripheral vision, without magnification, or with very small amounts of magnification, as well.

SUMMARY OF THE INVENTION

The present invention is an intraocular implant construction and method of production thereof.

According to the teachings of the present invention there is provided, an intraocular implant for implantation into the interior of a human eye, the eye having a retina, the implant comprising; (a) a body member, the body member having an anterior surface and a posterior surface, the body member having optical properties; and (b) an optical arrangement configured for forming a first image on the retina, the first image being an image of at least part of the central visual field, at least one of the body member and the optical arrangement being configured for forming a second image on the retina, the second image being an image of at least part of the peripheral visual field.

According to a further feature of the present invention, there is also provided at least one optical element configured for reducing or preventing, at least one of, overlap and over-spacing, of the first image and the second image on the retina.

According to a further feature of the present invention, there is also provided at least one optical element configured for adjusting the relative light intensity between the first image and the second image.

According to a further feature of the present invention, there is also provided: (a) at least one optical element configured for reducing or preventing, at least one of, overlap and over-spacing, of the first image and the second image on the retina; and (b) at least one optical element configured for adjusting the relative light intensity between the first image and the second image.

According to a further feature of the present invention, the optical arrangement includes at least two lenses, the two lenses defining an optical path between the two lenses, the optical arrangement including at least one mirror disposed externally to the optical path.

According to a further feature of the present invention, the optical arrangement includes at least two lenses and at least one mirror, the two lenses defining an optical path between the two lenses, the at least one mirror being disposed in the optical path.

According to a further feature of the present invention, the optical arrangement is configured such that, at least part of the light forming the second image crosses the path of at least part of the light forming the first image.

According to a further feature of the present invention, the optical arrangement is disposed at least partially within the body member.

According to a further feature of the present invention, the optical arrangement is completely surrounded by the body member.

According to a further feature of the present invention, the optical arrangement includes at least one mirror.

According to a further feature of the present invention, the optical arrangement includes a plurality of mirrors, each of the mirrors having a major surface which is configured for partially transmitting and partially reflecting light, the mirrors being arranged such that, light transmitted by one of the mirrors impacts the major surface of another of the mirrors.

According to a further feature of the present invention, the mirrors are configured to produce monocular stereopsys.

According to a further feature of the present invention, the optical arrangement includes a plurality of lenses.

According to a further feature of the present invention, the optical arrangement includes at least one lens and at least one mirror.

According to a further feature of the present invention, the optical arrangement includes at least one mirror having a surface which is configured for partially transmitting and partially reflecting light.

According to a further feature of the present invention, the optical arrangement includes at least one mirror having a first major surface configured for transmitting light and a second major surface configured for reflecting light.

According to a further feature of the present invention, the optical arrangement includes at least one mirror having a surface which is configured for partially transmitting and partially reflecting light.

According to a further feature of the present invention, the optical arrangement includes at least one lens, the lens including a reflective material disposed on at least one of, an external surface of the lens and an interior portion of the lens.

According to a further feature of the present invention, the body member has an inner portion and an outer portion.

According to a further feature of the present invention, the body member is at least partially foldable.

According to the teachings of the present invention there is also provided a method for improving vision, comprising the steps of: (a) providing an implant having a body member and an optical arrangement, the body member having an anterior surface and a posterior surface, the body member having optical properties, the optical arrangement being configured for forming a first image on the retina of an eye, the first image being an image of at least part of the central visual field, at least one of the body member and the optical arrangement being configured for forming a second image on the retina, the second image being an image of at least part of the peripheral visual field; and (b) implanting the implant into the eye.

According to a further feature of the present invention, there is also provided the step of implanting a conformer into the eye, wherein the step of implanting the implant is performed by inserting the implant into the conformer.

According to a further feature of the present invention, the step of implanting is performed while another intraocular lens is implanted in the eye.

According to a further feature of the present invention, the step of implanting is performed while the natural lens of the eye is still in the eye.

According to a further feature of the present invention, the step of implanting is performed by implanting the implant in a location in the eye, the location being selected from the group consisting of the capsular bag of the eye, the anterior chamber of the eye, the posterior chamber of the eye and the sulcus.

According to the teachings of the present invention there is also provided an intraocular implant for implantation into the interior of a human eye, the eye having a retina, the implant comprising an optical arrangement configured for forming an image on the retina of at least part of the central visual field, the optical arrangement including at least one light filter.

According to the teachings of the present invention there is also provided an intraocular implant for implantation into the interior of a human eye, the eye having a retina, the implant comprising an optical arrangement configured for forming an image on the retina of at least part of the central visual field, the optical arrangement including a first lens and a second lens, the first lens and the second lens defining a start and an end, respectively, of a light path through the implant, the first lens and the second lens being both concave or both convex.

BRIEF DESCRIPTION OF THE DRAWINGS

The invention is herein described, by way of example only, with reference to the accompanying drawings, wherein:

FIG. 21a is plan view of the intraocular implant of FIG. 1a having a plurality of internally mounted lens arrangements and a plurality of mirrors;

FIG. 21b is front view of the intraocular implant of FIG. 21a;

FIGS. 22a–22d are views of alternate embodiments of the intraocular implant of FIG. 1a having at least one internally mounted lens arrangement and a plurality of mirrors;

FIG. 31 is a view of the intraocular implant of FIG. 1a having a plurality of reflective coated lens disposed in the implant;

FIGS. 32a to 32g are views of coated lenses for use with the implant of FIG. 31;

FIG. 37 is a view showing a first method of manufacture of the intraocular implant of FIG. 1a; and FIG. 38 is a view showing a second method of manufacture of the intraocular implant of FIG. 1a.

DESCRIPTION OF THE PREFERRED EMBODIMENTS

The present invention is an intraocular implant construction and method of production thereof.

The principles and operation of an intraocular implant according to the present invention may be better understood with reference to the drawings and the accompanying description.

By way of introduction, the various embodiments of an intraocular implant according to the present invention are for use in the treatment of regular cataracts, and of disorders of central vision, as well as of disorders of peripheral vision. Additionally, the implant of the present invention is for use in treating AMD and other macular diseases, for example, but not limited to Retinitis Pigmentosa, Glaucoma and diseases causing impaired central or peripheral vision, such as Diabetic Retinopathy, Toxoplasmosis, non age-related Macular Degeneration and Solar Retinities.

Figure 1A:
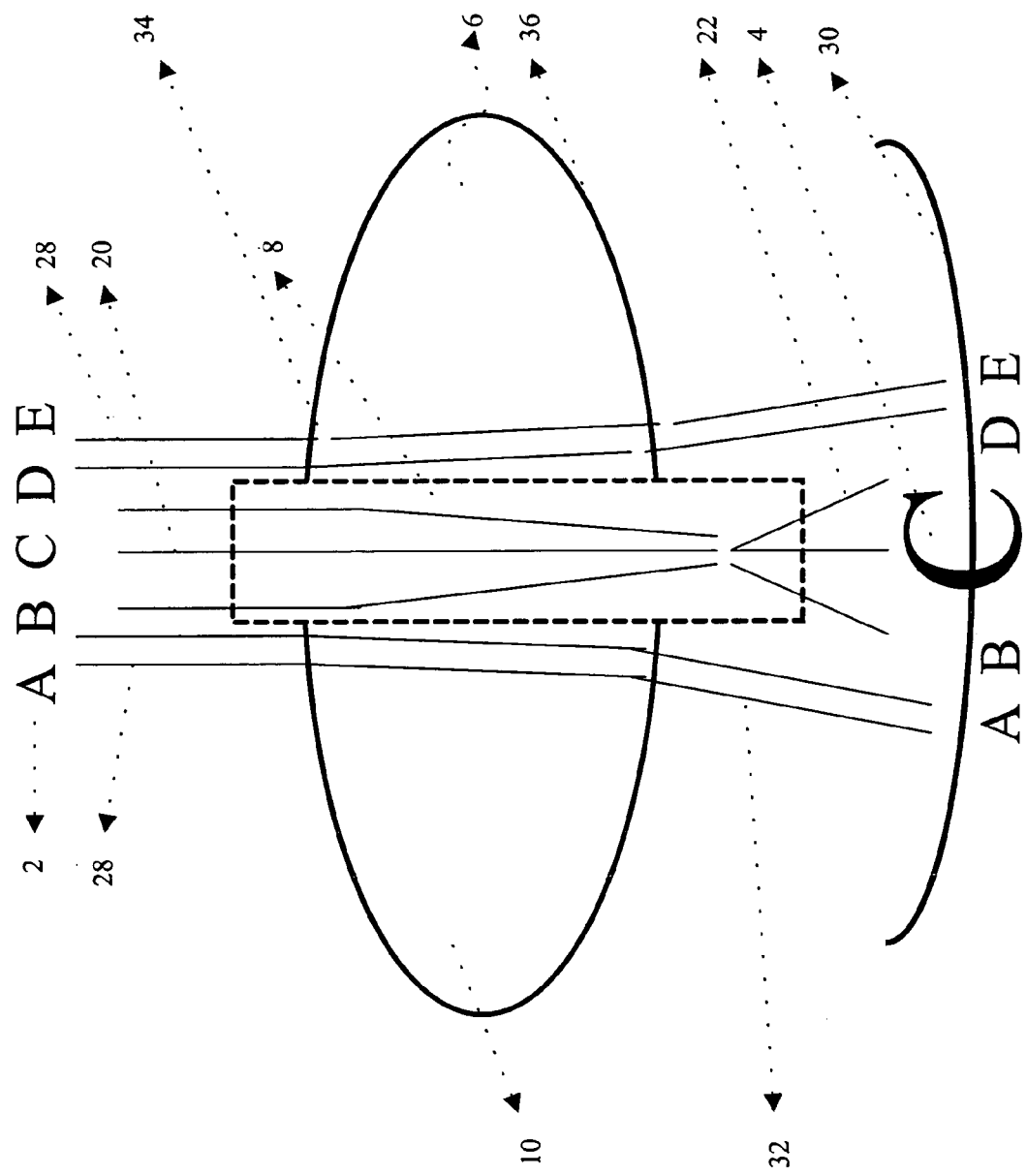
FIG. 1a is a sectional view of an intraocular lens implant that is constructed and operable in accordance with a preferred embodiment of the invention.

FIG. 1a is a sectional view of an intraocular lens implant 6 that is constructed and operable in accordance with a preferred embodiment of the invention. An object 2 is represented by the letters ABCDE (obviously this can be any image, picture, or even moving objects). The image produced on retina 30 is ABCDE (The letter "C" being enlarged). Implant 6 is a modified intraocular lens (hereinafter "IOL"). Prior art IOL implants are often used during cataract surgery. The loops that fixate implant 6 in the eye are not shown in FIG. 1. Fixation loops are shown with reference to the embodiments of FIGS. 4, 5, 23, 24, 25, 26, 27 and 30. It will be appreciated by those ordinarily skilled in the art that various designs and configurations of fixation loops can be used with the embodiments of the present invention. Additionally, the mode of fixating an IOL inside a human eye is known to those ordinarily skilled in the art of IOL implantation. It will be appreciated by those ordinarily skilled in the art that that lenses can be fixed in the eye as a one-piece element, where the loops and the lens formed as one piece or the implant can be formed from three or more elements. Implant 6 includes a central optical element 8, which is inserted inside an IOL body member lens 10. Lens 10 has an anterior surface 34, a posterior surface 36 and optical properties. Optical element 8 is configured for forming an image of the central visual field on retina 30. Lens 10, generally in conjunction with optical element 8, is configured for forming an image of the peripheral visual field on the retina. Peripheral light 28 passes through lens 10 and is projected onto the retina as light rays 32. Central optical element 8 includes a plurality of optical components configured to form a magnified or minified image on retina 30 of the central visual field. The optical components are typically a plurality of lenses or a plurality of mirrors or at least one lens and at least one mirror in combination in order to form a magnified or minified image of the central visual field. Central optical element 8 is represented by a cylinder in FIG. 1a. However, it will be appreciated by those ordinarily skilled in the art that the optical components of central optical component 8 do not need to be restricted to being disposed in a separate arrangement from lens 10. For example, the optical components of central optical component 8 can be disposed at least partially in lens 10 or on the surface of lens 10 or other arrangements as described in the various embodiments described hereinbelow. It will be appreciated by those ordinarily skilled in the art that the features of the embodiments described below can be combined together. It will be appreciated by those ordinarily skilled in the art that implant 6 can either be implanted in order to replace the natural lens of the eye (best shown in FIG. 24), can be implanted along with the natural lens of the eye still in place (best shown in FIG. 30) or be implanted in an eye already with an IOL as a secondary implant (best shown in FIGS. 25, 26 and 27). It will be appreciated by those ordinarily skilled in the art that lens 10 can be of any shape, but generally has a convexo-convexo or convexo-plano configuration. For example, anterior face 34 or posterior face 36 may be at least partially of convex, concave, plano, spherical, aspheric, irregular, asymmetric, astigmatic, prismatic, holographic or graded index configuration, or a combination thereof. The dioptric and other optical properties of lens 10 determine the visual correction of implant 6. Body member 10 is generally fabricated from the same material as conventionally used for making intraocular lenses, for example, but not limited to a transparent plastic (such as polymethylmethacrylate, acrylic, silicone, glass, sapphire or any other material suitable for use in the manufacturing and assembly of intraocular implants). It will be appreciated by those ordinarily skilled in the art that lens 10 can be made of a rigid material, a foldable material or a combination of both rigid and soft materials. For example, use of a material such as an acrylic or silicone allows implant 6 to be soft and foldable thereby enabling insertion of implant 6 through a small surgical incision. Implant 6 fills the entire lenticular capsular bag in certain configurations and applications, and does not need loops for fixation. In other configurations and applications implant 6 does not fill the entire lenticular capsular bag and needs loops of various configurations for fixing implant 6 inside the lenticular bag.

Figure 1B:
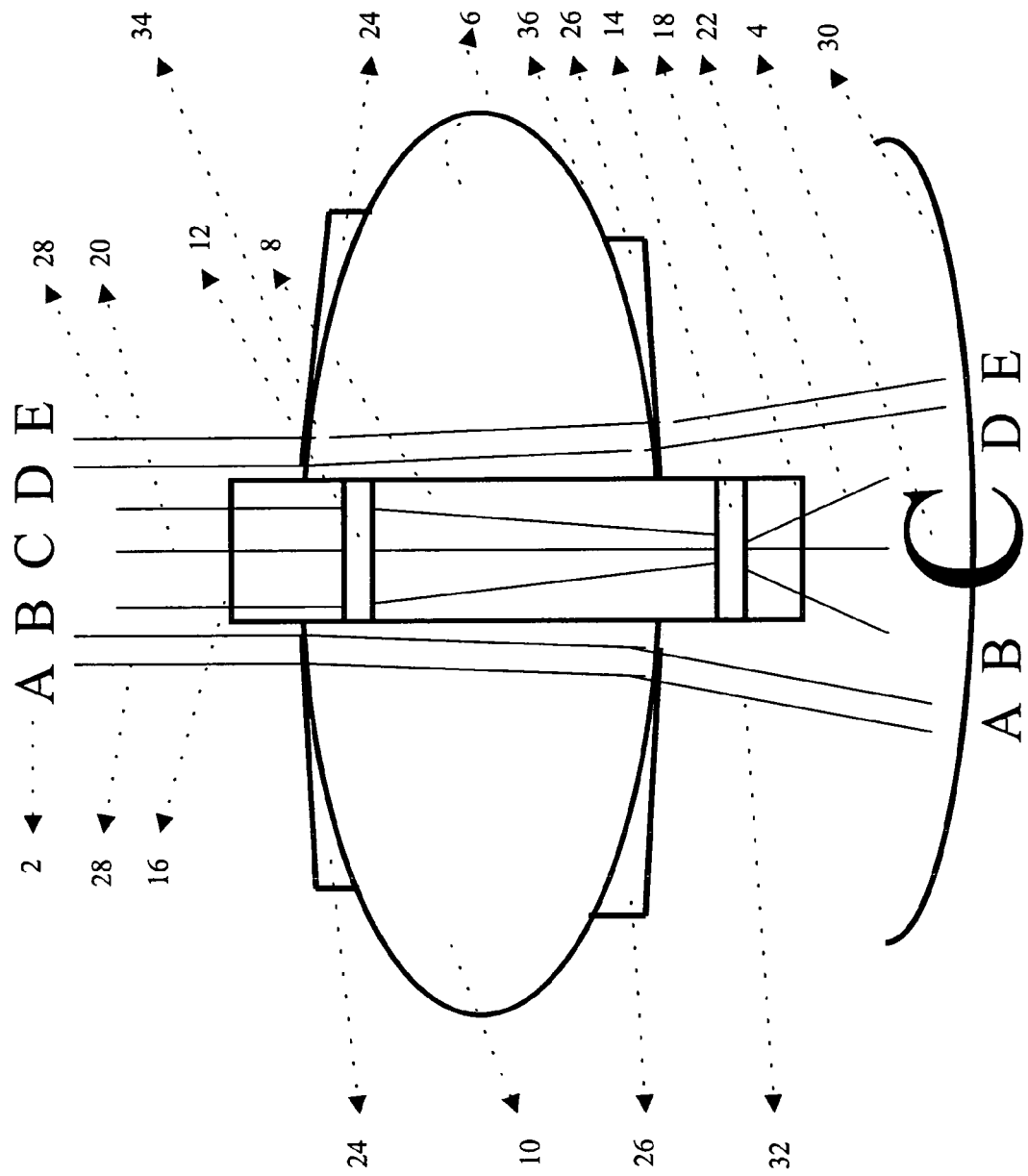
FIG. 1b is a sectional view of the intraocular lens implant of FIG. 1a configured to form a continuous image on the retina.

Reference is now made to FIG. 1b, which is a sectional view of intraocular lens implant 6 of FIG. 1a configured to form a continuous image on the retina so that the image of the central visual field and the peripheral visual field do not overlap or overlap as little as possible (nor that the image of the central visual field and the peripheral visual field are overly spaced apart). Central optical element 8 includes a cylinder having two lenses 12 and 14 disposed therein, defining a telescope arrangement. However, it will be appreciated by those ordinarily skilled in the art that element 8 can include just one or three or more lenses. The cylinder can be sealed at both ends by a seal 16 and a seal 18. Incoming light 20 passes through seal 16 and through the lenses 12, 14. The light emerges through seal 18. Central light rays 22 are projected on to retina 30. It will be appreciated by those ordinarily skilled in the art that any number of lenses can be disposed in the cylinder and that the dioptric power and the curvatures of the lenses can vary. It will be appreciated by those ordinarily skilled in the art that lenses 12, 14 can be spherical, aspherical and irregular in shape. Additionally, it will be appreciated by those ordinarily skilled in the art that lenses 12, 14 can be formed to produce: prismatic effects, a fresnel biprism, or holography. Furthermore, it will be appreciated by those ordinarily skilled in the art that lenses 12, 14 can be formed of a graded index material or lenses 12, 14 can have coatings that modify the transmission of light through the lenses. It will be appreciated by those ordinarily skilled in the art that lenses 12, 14 can be configured for, for example, but not limited to increasing or decreasing the image, visual field changes, changing the location of image formation on retina 30, or for improving or inducing optical aberrations. It will be appreciated by those ordinarily skilled in the art that seal 16, 18 can be flat with no dioptric power or can have any dioptric power as necessary for creating the enlarged image on the central area of the retina. It will be appreciated by those ordinarily skilled in the art that the cylinder of optical element 8 may vary in its size. Additionally, the cylinder of optical element 8 may protrude anteriorly and/or posteriorly from lens 10. Also optical element 8 can be filled with any material such as gas, air, liquids, or solid materials. Implant 6 of FIG. 1b also includes optical elements 24 and 26. Before passing through the anterior surface 34 of lens 10 light rays 28 pass through an optical element 24. After passing through the posterior surface 36 of lens 10, peripheral light 28 passes through optical element 26. Optical elements 24, 26 divert peripheral light 28 so that the peripheral image produced on the retina 30 is a continuation of the enlarged central image 4. This way, the central magnified image 4, shown by the letter C, and the peripheral image, shown by the letters ABDE, are continuous. In other words, the centrally magnified image, shown by the letter C is magnified and the peripheral visual field that is represented by letters ABDE are in direct continuity with the enlarged image C. Therefore, the patient sees the world in the way it is presented in image 4—a central enlarged image flush with, a normal size or slightly enlarged, peripheral visual field. Optical elements 24, 26 can be any element that displaces the light to the peripheral or any other area on the retina. Optical elements 24, 26 are for example, but not limited to a prisms, axicons, fresnels, holographic elements and graded index material elements. It will be appreciated by those ordinarily skilled in the art that optical elements 24, 26 can be formed integrally with, or disposed inside of, body member 10 of implant 6.

Figure 2:
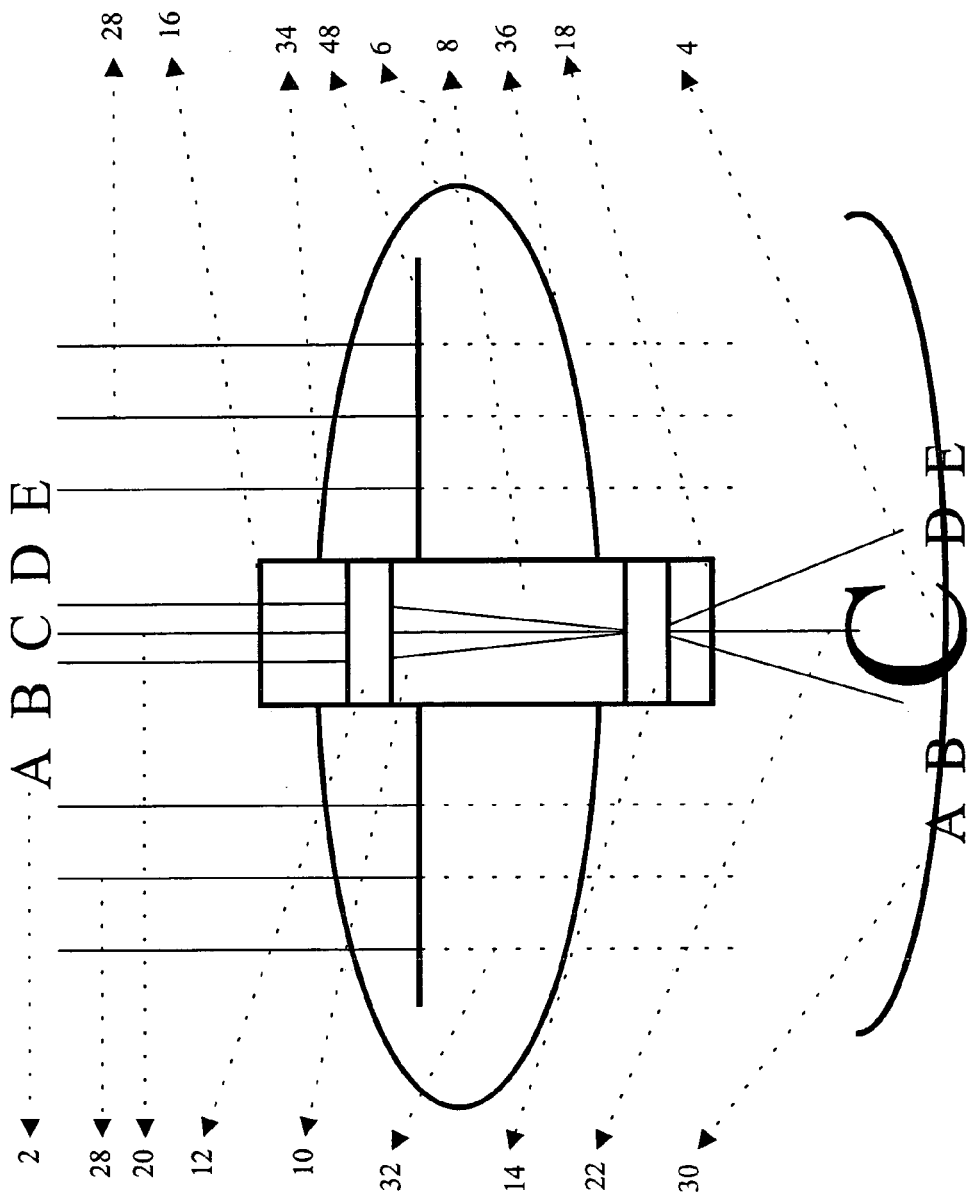
FIG. 2 is a view of the intraocular lens implant of FIG. 1a having a filter.

Reference is now made to FIG. 2, which is a view of intraocular lens implant 6 of FIG. 1a having one or more filters 48. According to this embodiment filter 48, is inserted so that it serves for regulating the light that passes through implant 6. Filter 48 is disposed so as to affect the peripheral field. However, it will be appreciated by those ordinarily skilled in the art that filter 48 can be disposed so as to affect the central and/or peripheral field. It will be appreciated by those ordinarily skilled in the art that filter 48 can be located anywhere inside or outside of implant 6, on anterior surface 34 or on posterior surface 36, or in any other location including inside optical element 8. One of the main reasons for using filter 48 is to regulate the amount of light that passes through implant 6 in order to adjust the relative light intensity between the central visual field image and the peripheral visual field image. There are several reasons why filter 48 is needed. For example, since we know that optical element 8 decreases the amount of light that reaches the retina 30 and we want the patient to see the central vision (in which there is less light) through optical element 8 clearly, filter 48 is added in order to decrease the amount of light of the peripheral vision. If filter 48 is not used the patient will see a bright periphery and a dark center, which may be the opposite result to the desired result. Therefore, by decreasing the amount of light in the periphery the patient may see a brighter magnified center and a mildly darker periphery, which will serve him better, since the center is damaged in a disease such as AMD. Furthermore filter 48 can be configured to prevent certain frequencies of lights from entering the eye. For example, filter 48 can prevent the penetration of UV light that damages retina 30. It will be appreciated by those ordinarily skilled in the art that filter 48 can be incorporated into any of the embodiments taught herein.

Figure 3:
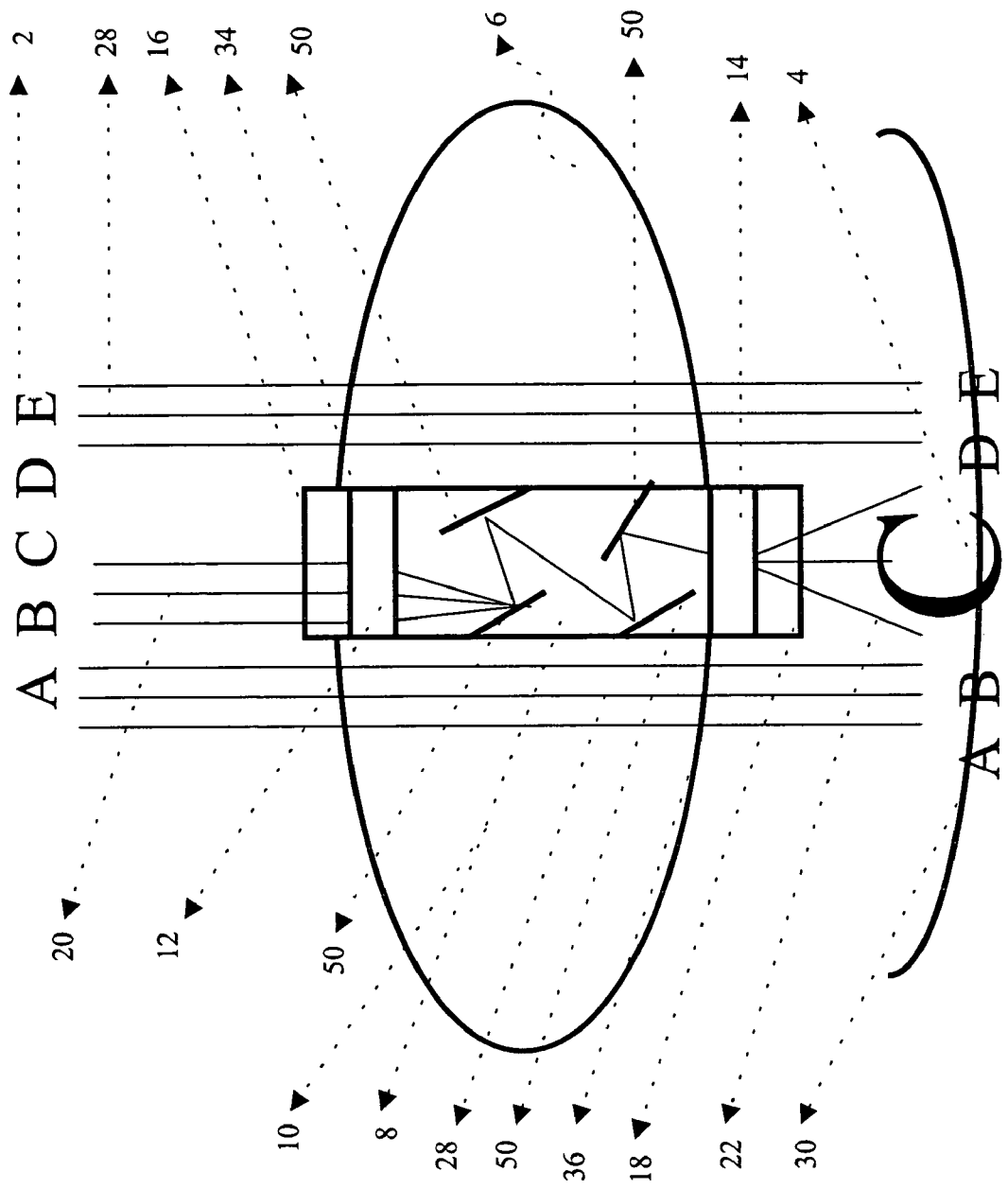
FIG. 3 is a view of the intraocular lens implant of FIG. 1a having a plurality of mirrors disposed in an optical element.

Reference is now made to FIG. 3, which is a view of intraocular lens implant 6 of FIG. 1a having a plurality of mirrors 50 disposed in optical element 8. Mirrors 50 are disposed inside optical element 8 between lenses 12 and 14, anteriorly to lens 12 or posteriorly to lens 14. In the present embodiment, light enters through seal 16, through lens 12, and then hits the first mirror 50. From the first mirror 50 the light continues to other optical elements (mirrors or lenses) and continues to pass through optical element 8. The light emerges through seal 18. After emerging from optical element 8, the central light 22 arrives at retina 30. The magnified, minified or displaced images are represented by reference numeral 4. It will be appreciated by those ordinarily skilled in the art that mirrors 50 can be any optical element having a reflecting surface, for example, but not limited to prisms. Furthermore, both lenses 12, 14 and mirrors 50 can be configured to transmit light (either partially or fully) or to absorb some frequencies of light or any combination thereof. Mirrors 50 are generally configured to increase the length of the path of the light through optical element 8 and therefore increase the telescopic effect of lenses 12, 14 without increasing the length of optical element 8. It will be appreciated by those ordinarily skilled in the art that lenses 12, 14 and mirrors 50 can be of any shape and that optical element 8 can be filled with air, gas, liquids or solid materials. It will be appreciated by those ordinarily skilled in the art that mirrors can be used without lenses, or lenses used without mirrors, or a single lens can be used with mirrors, or a single mirror can be used with lenses, or any combination of both mirrors and lenses.

Figure 4:
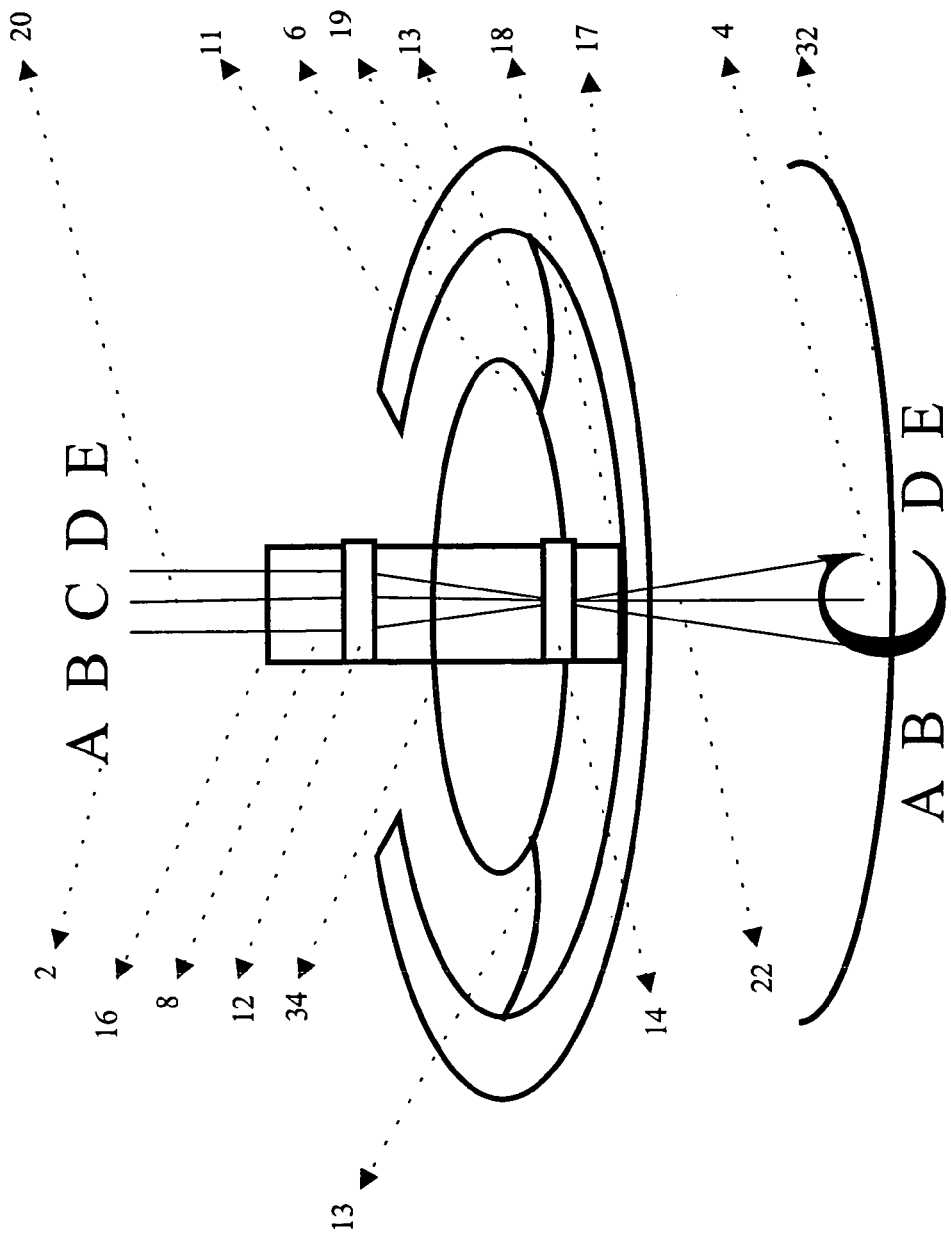
FIG. 4 is a view of the intraocular implant of FIG. 1a inserted into a conformer.
Figure 5:
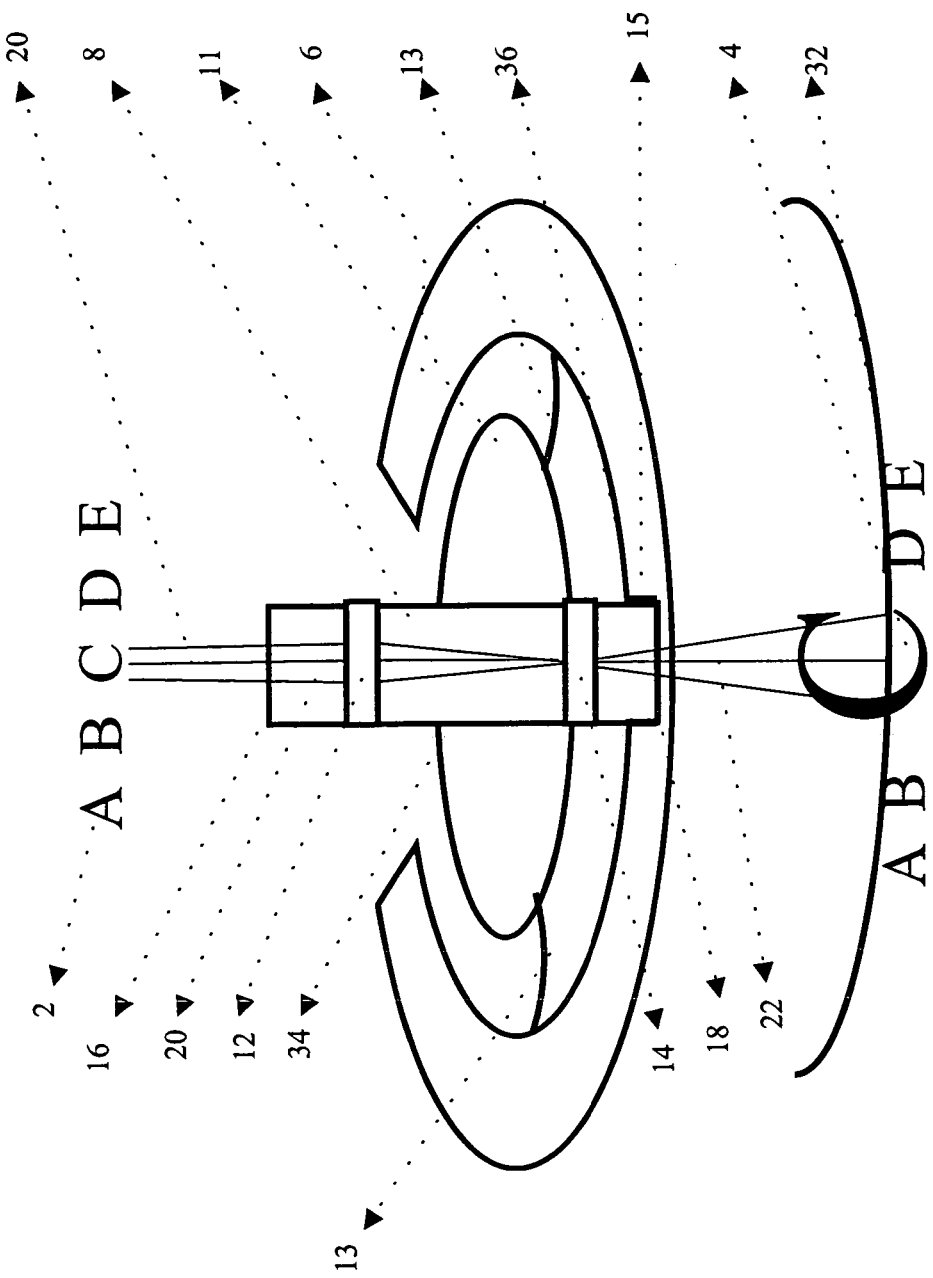
FIG. 5 is a view of the intraocular implant of FIG. 1a inserted into a conformer having a niche.

Reference is now made to FIG. 4, which is a view of intraocular implant 6 of FIG. 1a inserted into a conformer 11. Conformer 11 is first inserted into the capsule of the crystalline lens of the eye (for example, to replace the patient's lens after cataract surgery) and then the implant 6 is inserted into conformer 11 as an inner insert. This way, implant 6 is more easily replaced for another more suitable implant as the underlying disease changes and progresses. Additionally, the position of implant 6 and/or optical element 8 is adjustable from outside the eye. Optionally, another mechanism for rotating implant 6 within conformer 11 can be included. It will be appreciated by those ordinarily skilled in the art that conformer 11 can include optical components such as one or more lenses and/or mirrors, or conformer 11 can have optical properties itself. It will be appreciated by those ordinarily skilled in the art that conformer 11 can be formed from hard (non-foldable) or soft (foldable) materials. Additionally, conformer 11 can be placed in any structure of the eye, but preferably into the lenticular capsule. Furthermore, conformer 11 can have one or more loops (not shown) for fixing conformer 11 to the eye structure. Optionally, conformer 11 may be configured to be implanted without loops by filling the capsular bag. Conformer 11 can be implanted in other sites in the eye such as the vitreous, iris support, anterior chamber or posterior chamber. Implant 6 is typically disposed inside conformer 11 so that the posterior edge of optical element 8 touches conformer 11. Implant 6 is typically attached to conformer 11 by one or more loops 13, as in normal IOL's. It will be appreciated by those ordinarily skilled in the art that implant 6 can fill the whole volume of conformer 11 thereby negating the necessity for loops 13. Conformer 11 has two surfaces, an outer surface 17 which is in contact with the capsular bag and an inner surface 19 which defines the space where implant 6 is located, with or without loops 13. Surfaces 17 and 19 can have any suitable shape and optical properties. It will be appreciated by those ordinarily skilled in the art that conformer 11 can be used with any of the embodiments described herein. Reference is now made to FIG. 5, which is a view of intraocular implant 6 of FIG. 1a inserted into conformer 11 having a niche 15. Niche 15 is configured for stabilizing the position of implant 6 within the eye for example for preventing tilt of implant 6 which could distort the central vision. It will be appreciated by those ordinarily skilled in the art that niche 15 can be wider or narrower than the posterior width of implant 6.

Figure 6:
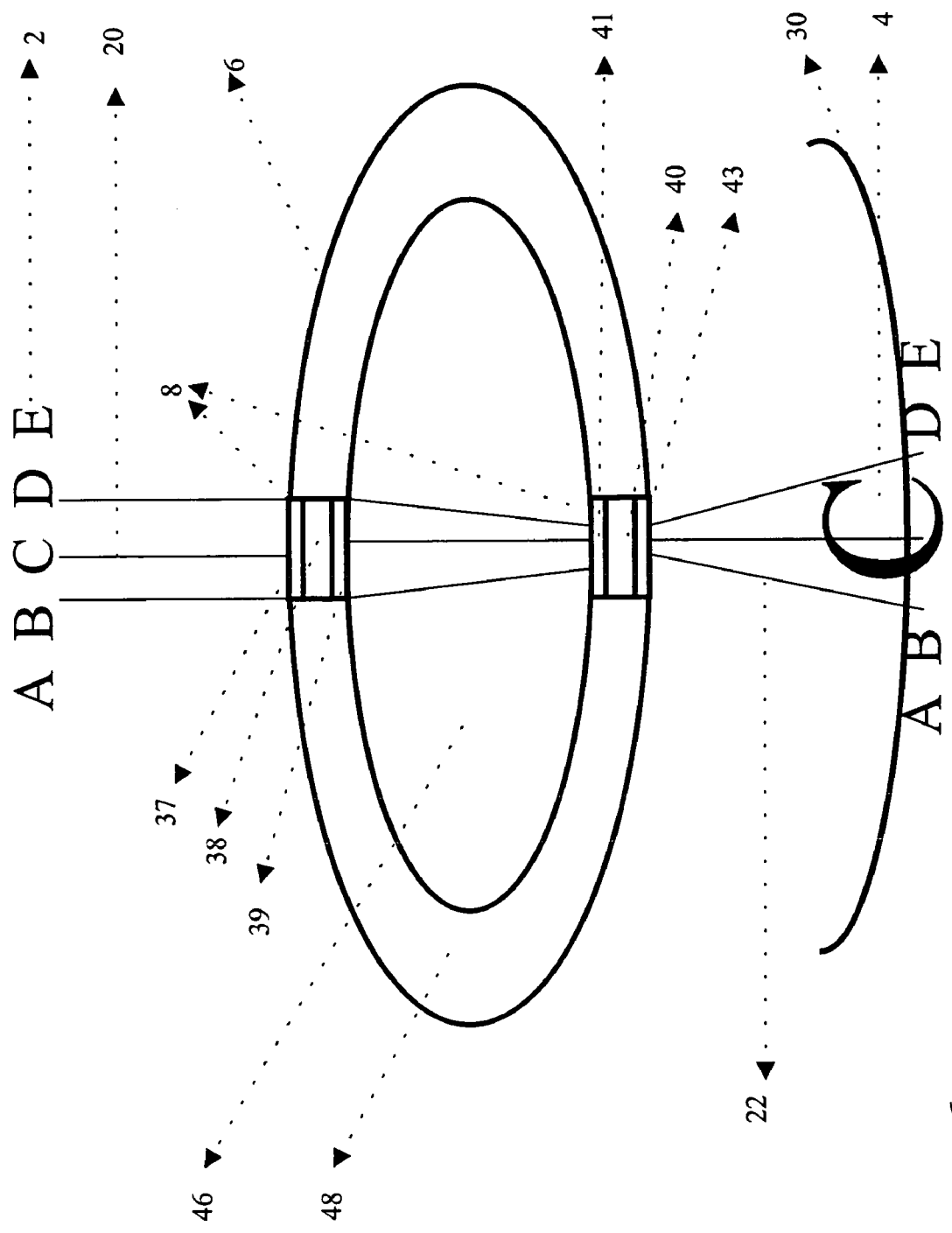
FIG. 6 is a view of the intraocular implant of FIG. 1a having a split central optical element.

Reference is now made to FIG. 6, which is a view of intraocular implant 6 of FIG. 1a having a split central optical element 8. In this embodiment, lens 10 has an outer portion 48 and an inner portion 46. It will be appreciated by those ordinarily skilled in the art that portions 46 and 48 can be formed from the same or different materials having the same or different refractive indices. The differences refractive indices may create an optical effect. It will be appreciated by those ordinarily skilled in the art that portion 46 may be an air filled cavity. Central cavity 46 may be filled with gas, liquid, and solid materials and may even contain more than one material or a combination of materials. Cavity 46 may also be filled with the same materials used to form outer portion 48. In this embodiment, central optical element 8 is split into two portions an anterior portion 38 and a posterior portion 40. Central optical element 8 does not have a connecting cylinder that extends from one side of implant 6 to the other. It has numerous advantages including, but not limited to, the possibility of peripheral light passing through the middle of central optical element 8. Therefore, some of the peripheral light crosses the path of at least some of the central visual field light. Anterior portion 38 includes lenses 37 and 39. Posterior portion 40 includes lenses 41 and 43. However, it will be appreciated by those ordinarily skilled in the art that portions 38 and 40 can include any combination of lenses, mirrors, prisms, or other optical elements. It will be appreciated by those ordinarily skilled in the art that the cavity between lenses 37, 39 and 41, 43 can be unfilled or can filled with any material. It will be appreciated by those ordinarily skilled in the art that portions 38 and 40 can be identical in their geometry or different in their shape, number, cavities, or any other properties. In operation, the central light 20 passes through portion 38 and continues through inner portion 46 and passes through portion 40, and then emerges as central light 22, which arrives at the center of retina 30. FIG. 6 does not demonstrate the path of the peripheral light, but it is clear that peripheral light passes from all sides and is affected by differences that may be between the refractive indices of the materials of portions 46 and 48. It will be appreciated by those ordinarily skilled in the art that the shapes and/or the relative refractive indices of portions 46 and 48 can be configured to produce a continuous image of the central and peripheral vision on retina 30.

Figure 7A:
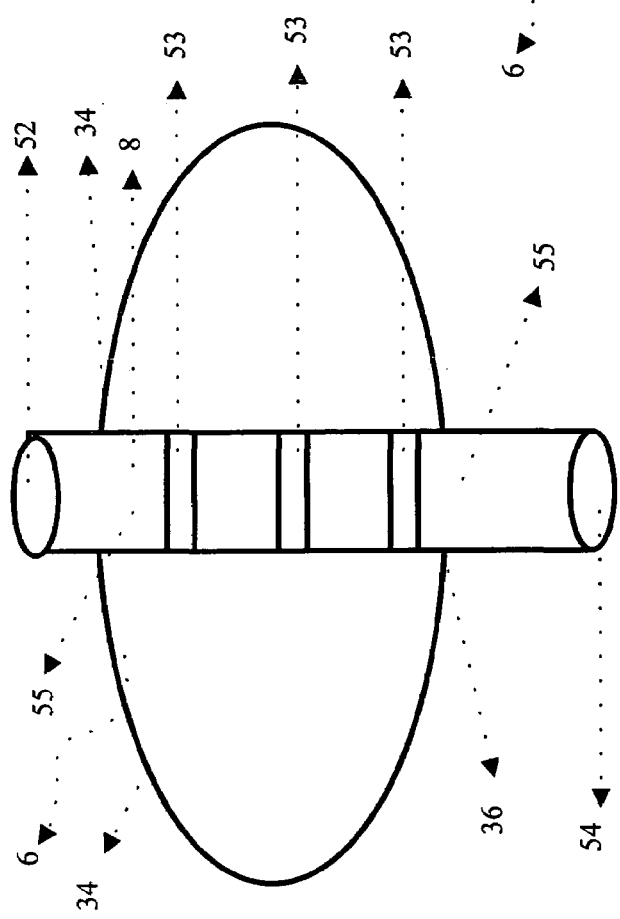
FIG. 7a is a view of the intraocular implant of FIG. 1a showing a first preferred embodiment of the central optical element.

Reference is now made to FIG. 7a, which is a view of intraocular implant 6 of FIG. 1a showing a first preferred embodiment of central optical element 8. Central optical element 8 has an anterior convex lens 52 and a posterior convex lens 54 and a cavity 55. Lens 52 and lens 54 define a start and an end, respectively, of a light path through implant 6. A plurality of lenses 53 are disposed in cavity 55 between lenses 52 and 54. It will be appreciated by those ordinarily skilled in the art that lenses 53 can be either concave or convex or a combination of the two. It will be appreciated by those ordinarily skilled in the art that lenses 53 can be of many kinds, including, but not limited to, convex, concave, plano, spherical, aspheric, irregular, asymmetric, astigmatic, prismatic, holographic or graded index configuration, or any combination thereof. It will be appreciated by those ordinarily skilled in the art that the power and form of lenses, 52, 53, 54 are chosen to magnify or minify and/or displace the central image or improve optical aberrations. Cavity 55 is typically filled with any material, including air, gas, liquid, solid. It will be appreciated by those ordinarily skilled in the art that cavity 55 can be unfilled or filled with more than one material.

Figure 7B:
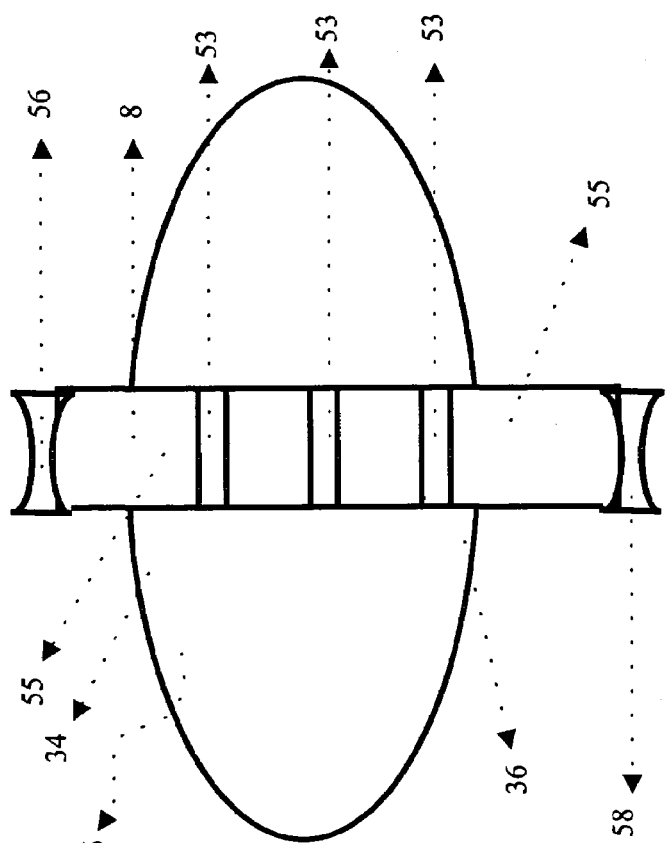
FIG. 7b is a view of the intraocular implant of FIG. 1a showing a second preferred embodiment of the central optical element.

Reference is now made to FIG. 7b, which is a view of intraocular implant 6 of FIG. 1a showing a second preferred embodiment of central optical element 8. This embodiment is the same as the embodiment described with reference to FIG. 7a, except that outside lenses 56, 58 are both concave. Central optical element 8 has a cavity 55 closed by anterior concave lens 56 and posterior concave lens 58. A plurality of lenses 53 are disposed in cavity 55 between lenses 56 and 58.

Figure 8:
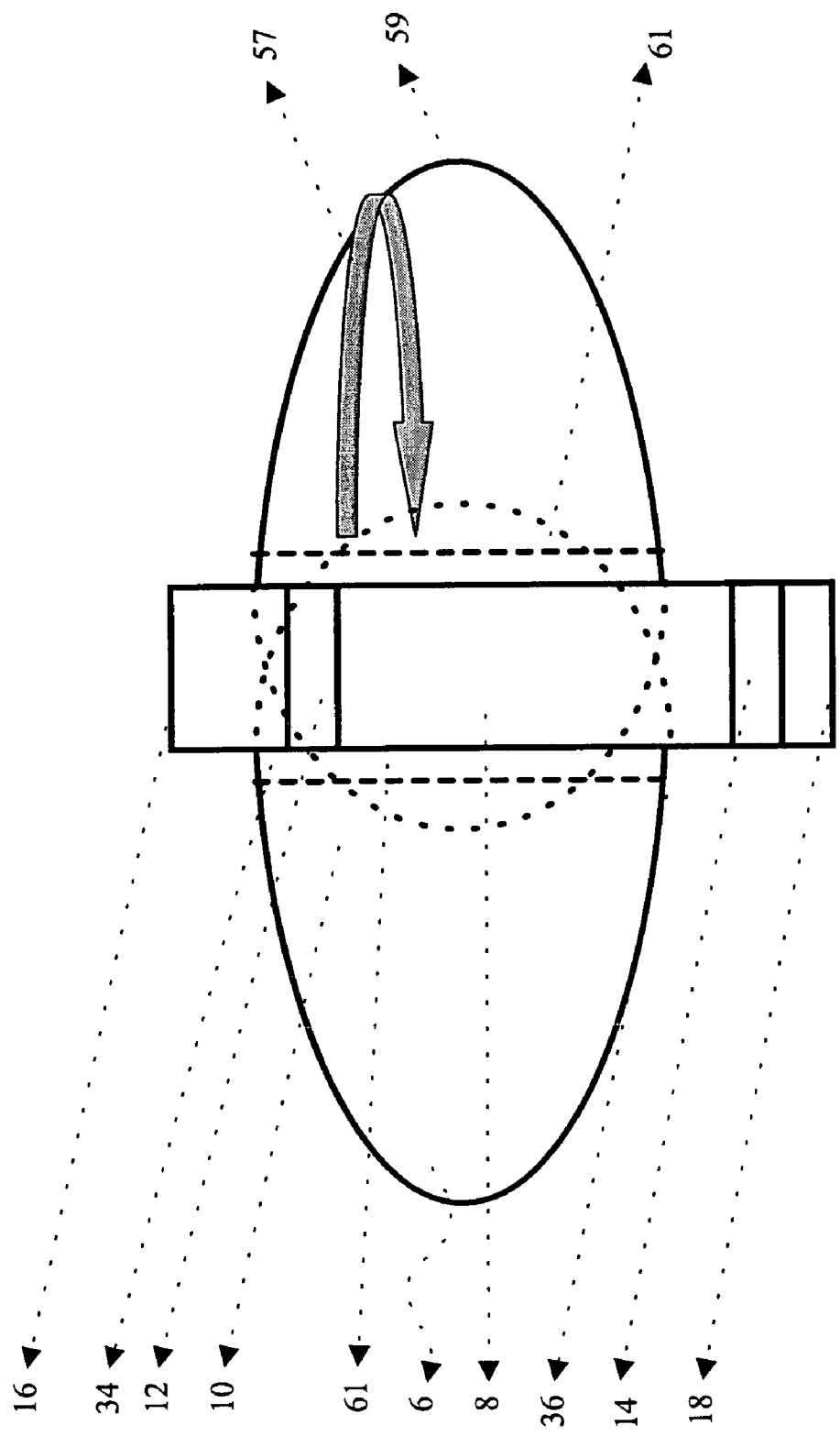
FIG. 8 is a view of the intraocular implant of FIG. 1a showing how the implant is foldable.

Reference is now made to FIG. 8, which is a view of intraocular implant 6 of FIG. 1a showing how implant 6 is foldable. Preferably, lens 10 is made of foldable material, so that implant 6 is foldable and can be inserted into the eye through a small incision. Arrow 57 indicates the way implant 6 is folded so that the peripheral part 59 of lens 10 is folded to the position shown by dotted line 61.

Figure 9:
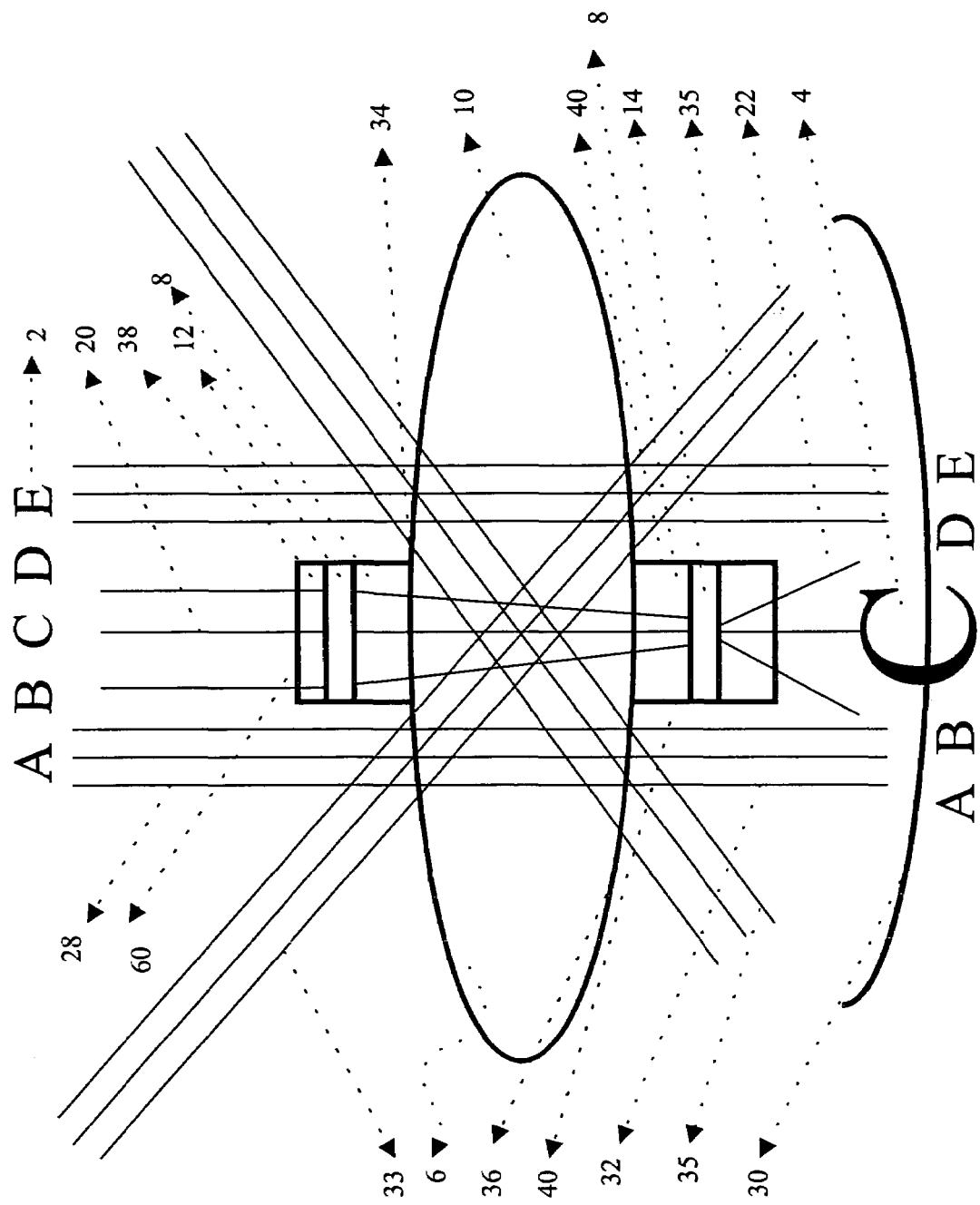
FIG. 9 is a view of the intraocular implant of FIG. 1a having a split externally mounted central optical element.

Reference is now made to FIG. 9, which is a view of intraocular implant 6 of FIG. 1a having a split externally mounted central optical element 8. In this embodiment, central optical element 8 is split into two portions an anterior portion 38 and a posterior portion 40. Central optical element 8 does not have a connecting cylinder that extends from one side of implant 6 to the other. Therefore, peripheral light 28 passes through implant 6 and emerges as 32. Also, light 33 that is coming from the side passes through body member 10 emerging as 35 without interference of a central cylinder thereby providing the patient with a good peripheral image. Portion 38 is mounted on anterior surface 34 of lens 10 and portion 40 is mounted on posterior surface 36 of lens 10. Anterior portion 38 includes lens 12. Posterior portion 40 includes lens 14. The outer housing of portions 38, 40 is typically formed from glass or other transparent material such as transparent plastic (e.g. polymethylmethacrylate, acrylic, or silicone), sapphire or any other material suitable for use in the construction of intraocular implants. Lenses 12 and 14 are typically convex, concave, plano, spherical, aspheric, irregular, asymmetric, astigmatic, prismatic, holographic or graded index configuration, or some combination thereof. It will be appreciated by those ordinarily skilled in the art that portions 38 and 40 can contain more than one lens. Portions 38, 40 can be filled with air or any other material such as solids, gases or liquids. The anterior surface 60 of portion 38 is typically plano. However, it will be appreciated by those ordinarily skilled in the art that surface 60 can have any dioptric power. In operation, central light 20 first passes through portion 38 and then through lens 10. From there, central light 20 passes through portion 40. After passing through portion 40, the light arrives at retina 30. It will be appreciated by those ordinarily skilled in the art that portions 38 and 40 may be identical or different. It will be appreciated by those ordinarily skilled in the art that at least one of portions 38 and 40 can be disposed at least partially within the surface of lens 10.

Figure 10:
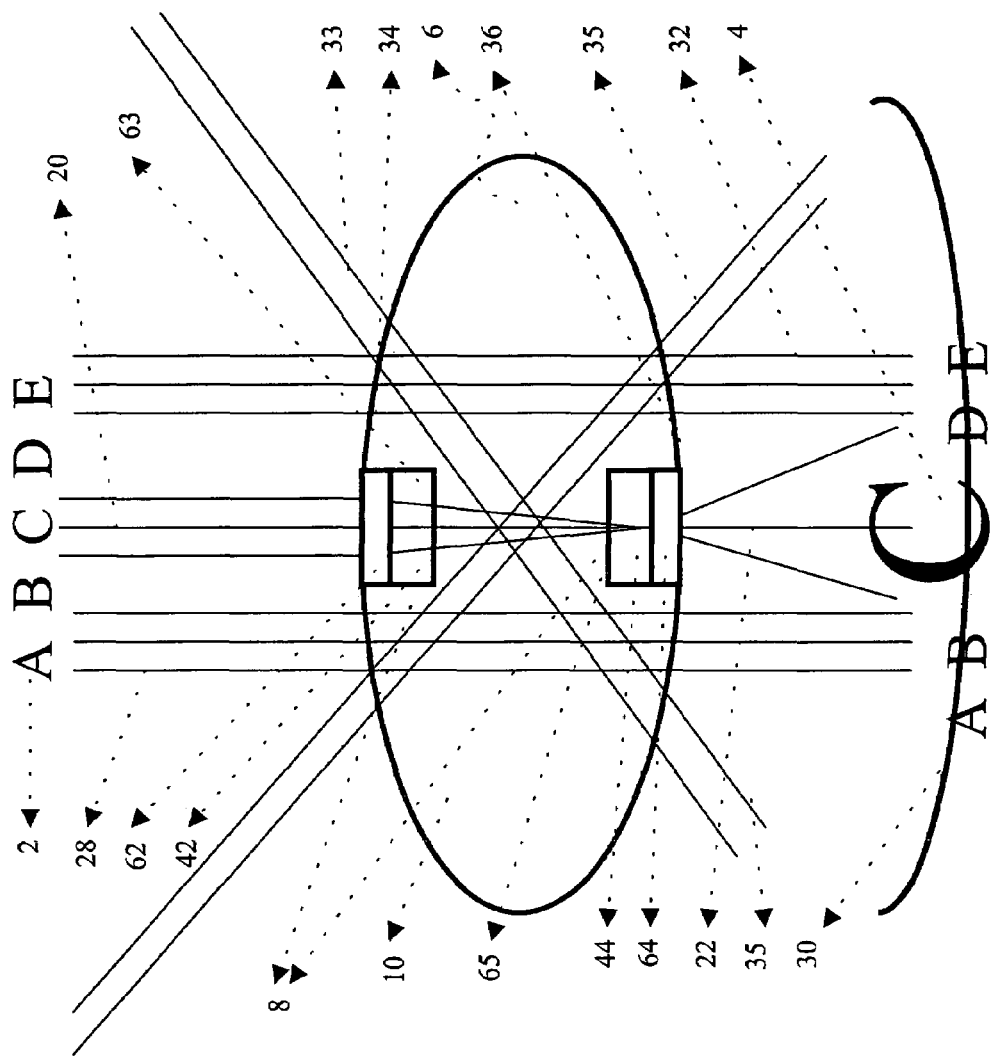
FIG. 10 is a view of the intraocular implant of FIG. 1a having a split internally mounted central optical element.

Reference is now made to FIG. 10, which is a view of intraocular implant 6 of FIG. 1a having a split internally mounted central optical element 8. Central optical element 8 is formed by covering cylindrical holes 42 and 44 in the anterior and posterior of lens 10 with lenses 62 and 64, respectively. The cavities of holes 42, 44 are typically filled with air or any other material such as a solid, liquid or gas. It will be appreciated by those ordinarily skilled in the art that one or more lenses and/or mirrors can be disposed in holes 42, 44. It will be appreciated by those ordinarily skilled in the art that the surfaces 63 and 65 of holes 42 and 44, respectively, can also have an optical power, which is created by the curvature of surfaces 63 and 65, respectively and the differences in refractive indices between the cavities of holes 40, 42 and lens 10.

Figure 11:
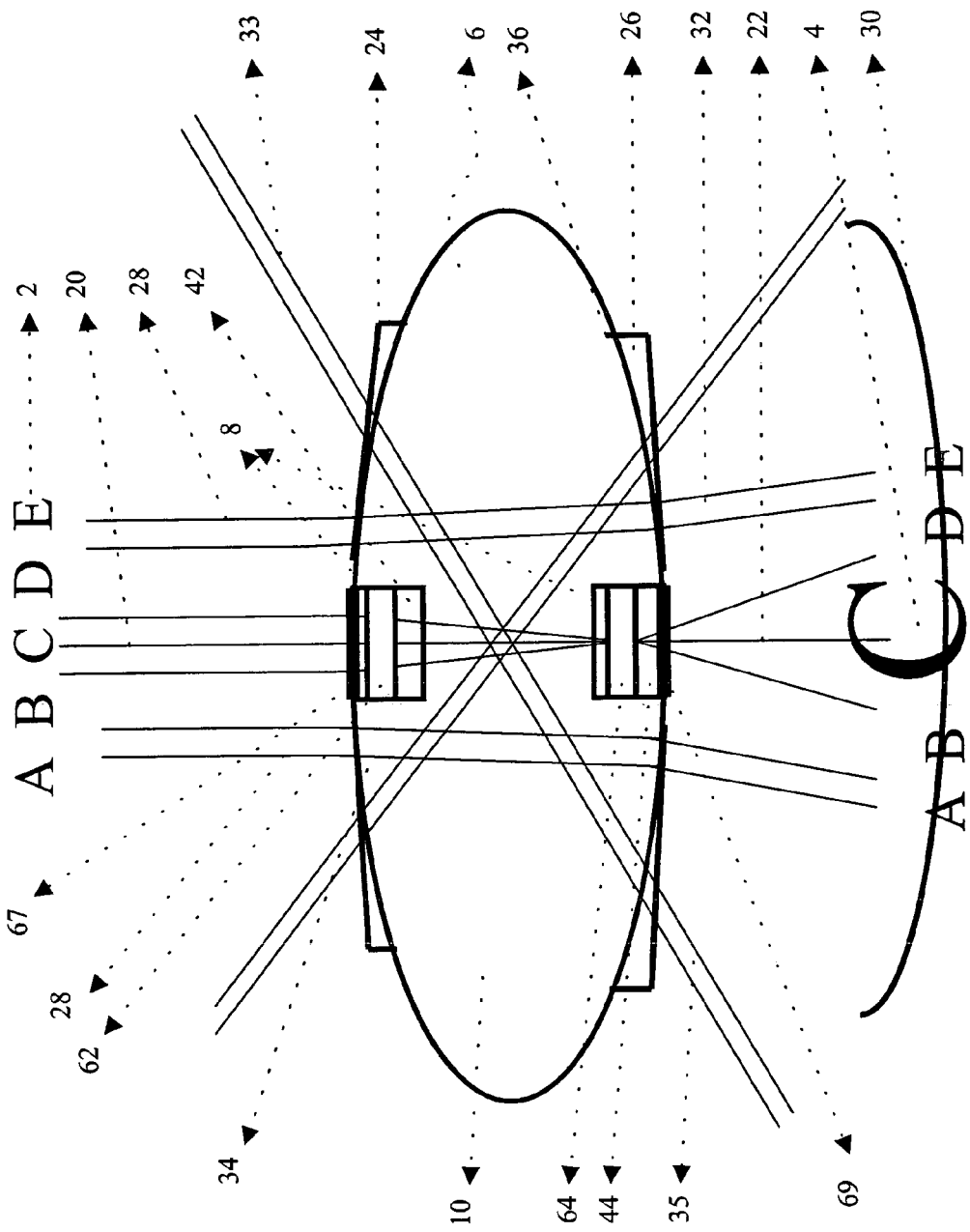
FIG. 11 is a view of the intraocular implant of FIG. 1a having a split internally mounted central optical element configured to form a continuous image on the retina.

Reference is now made to FIG. 11, which is a view of intraocular implant 6 of FIG. 1a having a split internally mounted central optical element 8, implant 6 being configured to form an image that is at least partially continuous on retina 30. Central optical element 8 is formed by covering cylindrical holes 42 and 44 in the anterior and posterior of lens 10 with seals 67 and 69, respectively. Lenses 62 and 64 are inserted into the cavities of holes 42 and 44, respectively. Implant 6 contains two optical elements 42 and 44 that are similar to what was shown in FIG. 10. Seals 67, 69 are either flush with, or protrude from, the anterior surface 34 and posterior surface 36, respectively. Seals 67, 69 are typically formed from glass, PMMA, or any other solid material. Optical elements 24, 26 divert the peripheral light in such a way that the central magnified image C is at least partially continuous with the peripheral image, as described with reference to FIG. 1b.

Figure 12:
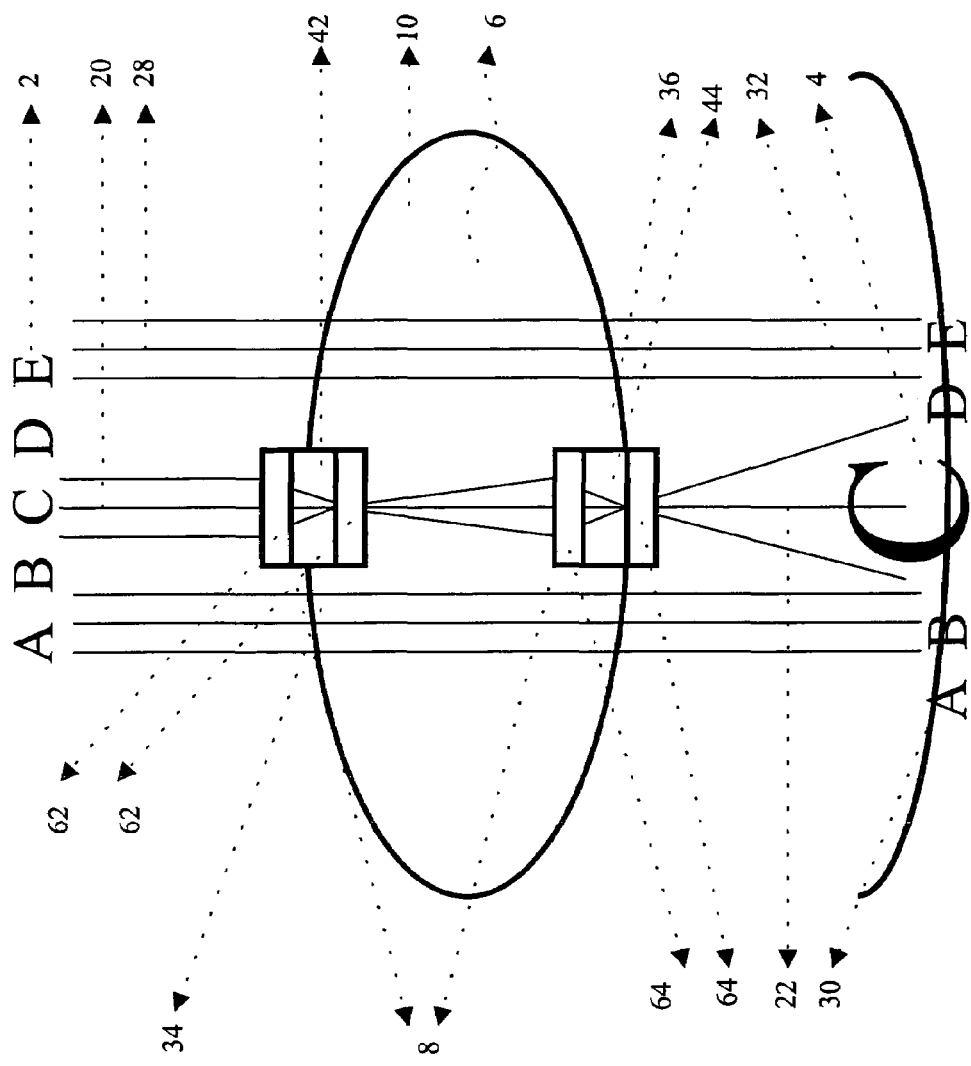
FIG. 12 is a view of the intraocular implant of FIG. 1a having a split partially internally mounted central optical element.

Reference is now made to FIG. 12, which is a view of intraocular implant 6 of FIG. 1a having a split partially internally mounted central optical element 8. Central element 8 is partially embedded inside lens 10 and partially protruding from lens 10 both from the anterior and posterior of lens 10.

Figure 13:
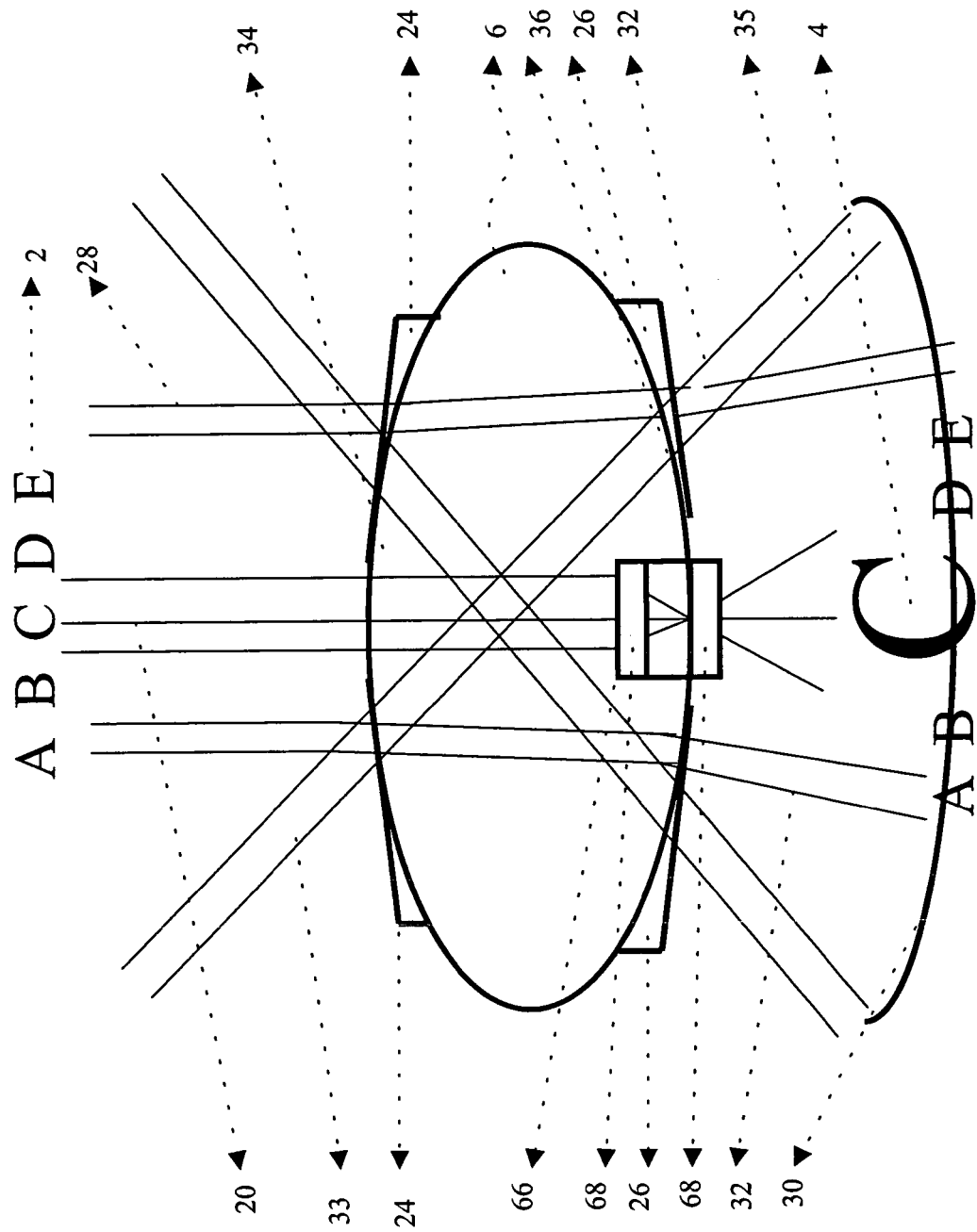
FIG. 13 is a view of the intraocular implant of FIG. 1a having a single partially internally mounted central optical element, the implant being configured to form a continuous image on the retina.

FIG. 13 is a view of intraocular implant 6 of FIG. 1a having a single partially internally mounted central optical element 66, implant 6 being configured to form a continuous image on retina 30. Implant 6 includes optical elements 24 and 26 in order to form a continuous image on retina 30 as described with reference to FIG. 1a. The central light entering the eye passes through the center of lens 10 then passes through optical element 66, and from optical element 66 the light reaches retina 30. It will be appreciated by those ordinarily skilled in the art that optical element 66 can contain one or more lenses 68 and one or more mirrors (not shown). One of the advantages of this embodiment is that there is minimal disturbance to the peripheral light 33 that comes from the sides when passing through the device since it does not hit any cylinder or mirror that disturbs in its path.

Figure 14:
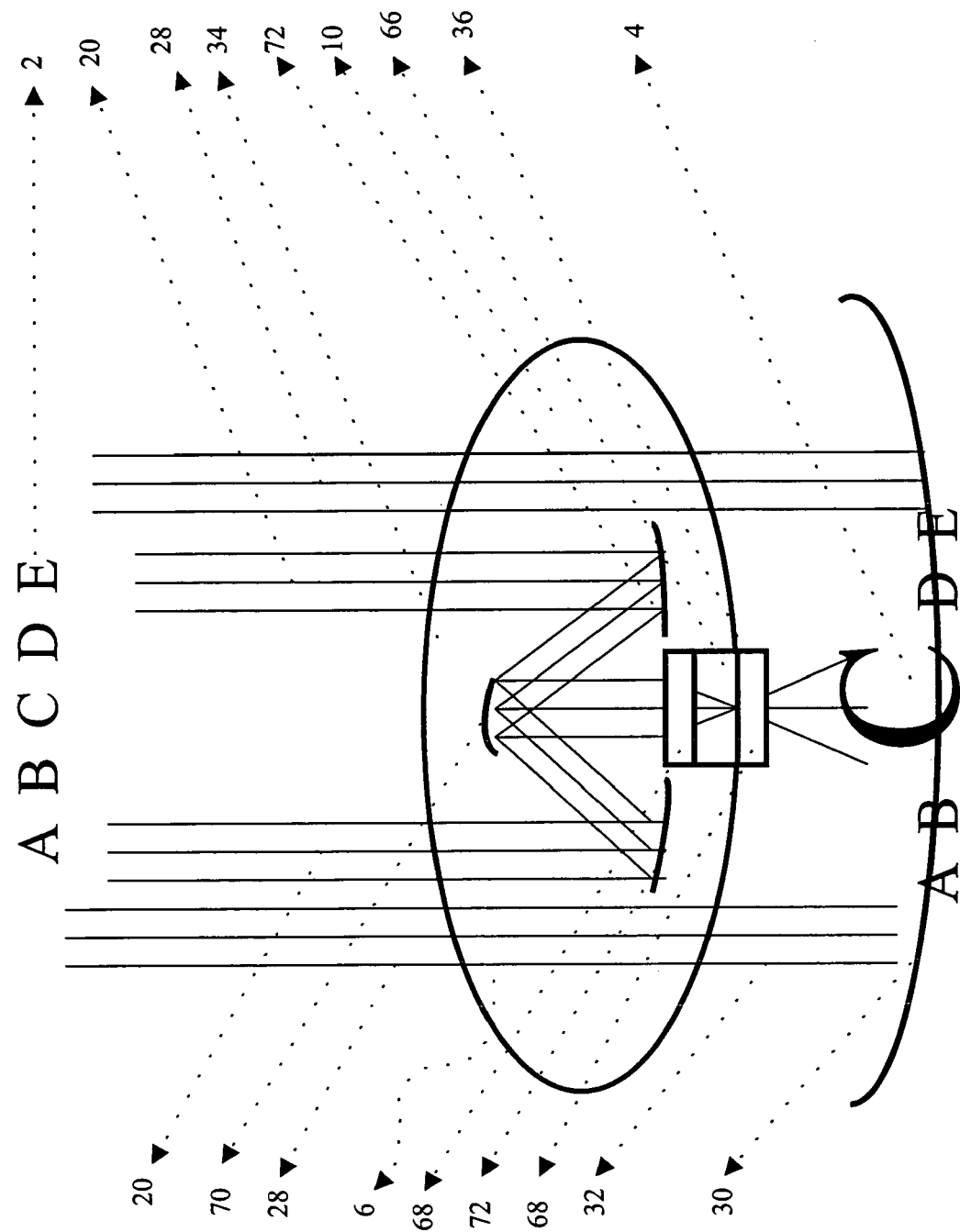
FIG. 14 is a view of the intraocular implant of FIG. 1a having a partially internally posteriorly mounted central lens arrangement with a plurality of mirrors.

Reference is now made to FIG. 14, which is a view of intraocular implant 6 of FIG. 1*a* having a partially internally posteriorly mounted central lens arrangement 66 with a plurality of mirrors 70, 72. Mirrors 70, 72 form a Cassegrain telescope which is combined with optical element 66. It will be appreciated by those ordinarily skilled in the art that any other combination of mirrors with optical element 66 can be used. Optical element 66 is placed posteriorly in lens 10. It will be appreciated by those ordinarily skilled in the art that optical element 66 can also be placed anteriorly or inside lens 10. Element 66 is typically hollow or filled with any material. Optical element 66 typically includes one or more lenses 68 and one or more mirrors (not shown). It will be appreciated by those ordinarily skilled in the art that lenses 68 can be of many kinds, including, but not limited to convex, concave, piano, spherical, aspheric, irregular, asymmetric, astigmatic, prismatic, holographic or graded index configuration, or some combination thereof. It will be appreciated by those ordinarily skilled in the art that mirrors 70, 72 can be convex or concave, rounded or pointed and therefore take various shapes including spherical and aspheric shapes. In operation, central light which enters implant 6 reflects off mirror 72 toward central mirror 70. The light is then reflected by mirror 70 through optical element 66. The light emerges from element 66 and is projected onto retina 30 as image 4, creating an increased or minified image on the center of the retina. Peripheral light 28 enters implant 6 and emerges as 32 before reaching the retina. It will be appreciated by those ordinarily skilled in the art that implant 6 can include a mirror telescope, created by mirrors 70 and 72 and a lens telescope (Galilean or another telescope) or any combination and configuration of mirrors and lenses.

Figure 15:
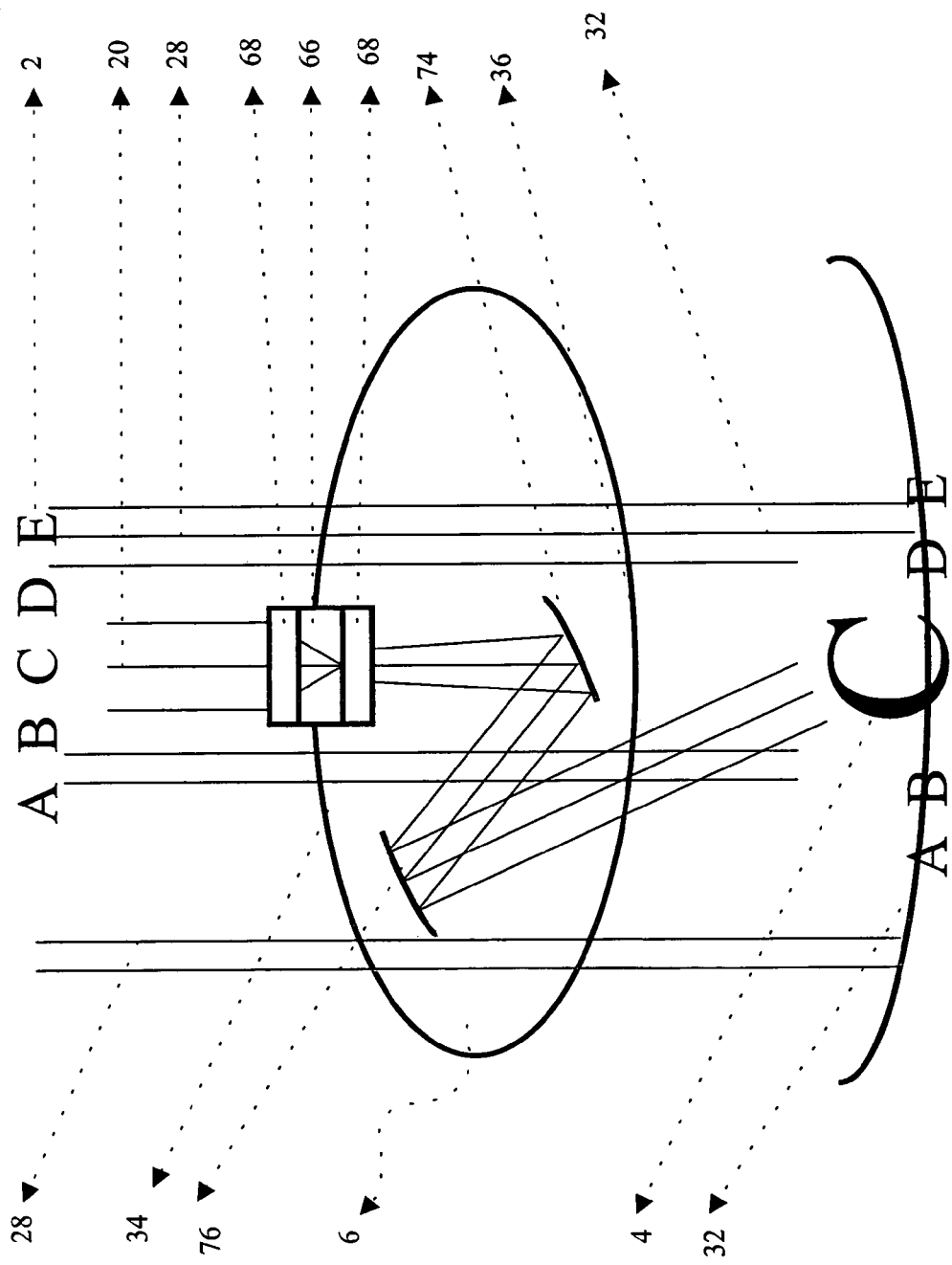
FIG. 15 is a view of the intraocular implant of FIG. 1a having a partially internally anteriorly mounted central lens arrangement with a plurality of off-axis mirrors.

Reference is now made to FIG. 15, which is a view of intraocular implant 6 of FIG. 1*a* having a partially internally anteriorly mounted central lens arrangement 66 with a plurality of mirrors 74, 76. Mirrors 74 and 76 direct central light after it passes through optical element 66. The mirror configuration is a non-limiting example for an "off axis" optical system, which includes at least two mirrors, mirror 74 located in the center, and mirror 76 located in the periphery.

Figure 16:
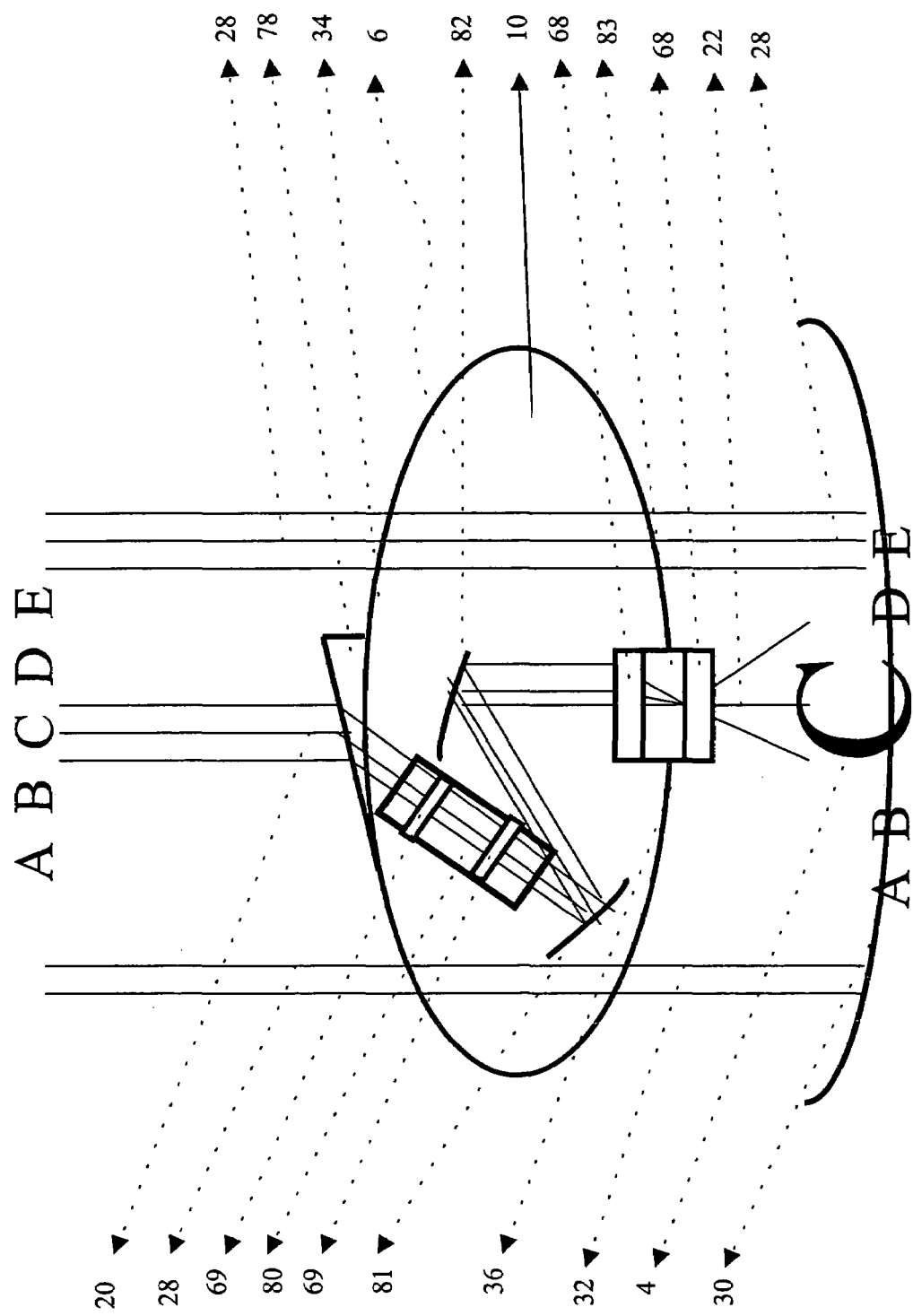
FIG. 16 is a view of the intraocular implant of FIG. 1a having a partially internally anteriorly mounted central lens arrangement, an internally mounted lens arrangement and a plurality of off-axis mirrors.

Reference is now made to FIG. 16, which is a view of intraocular implant 6 of FIG. 1*a* having a partially internally posteriorly mounted central lens arrangement 83, an internally mounted lens arrangement 80 and a plurality of off-axis mirrors 81, 82. Implant 6 also includes optical element 78. Optical element 78 is configured for directing entering light 20 towards mirror 81. It will be appreciated by those ordinarily skilled in the art that optical element 78 can include prisms, fresnel, holography or graded index material. Lens arrangement 80, which is disposed between optical element 78 and mirror 81 typically includes one or more lenses 69 and optionally one or more mirrors. Similarly, lens arrangement 83 typically includes lenses 68 and one or more mirrors. Central light 20 enters the implant through optical element 78, which directs the light to element 80. After passing through element 80, central light is reflected from mirrors 81 and 82 before reaching element 83 and emerging as light 22. Light 22 is projected onto retina 30 and creates an image 4, which is either magnified or minified, depending on the optical components chosen and the condition that the patient is suffering from. Peripheral light 28 emerges from lens 10 as light 32 before reaching retina 30.

Figure 17:
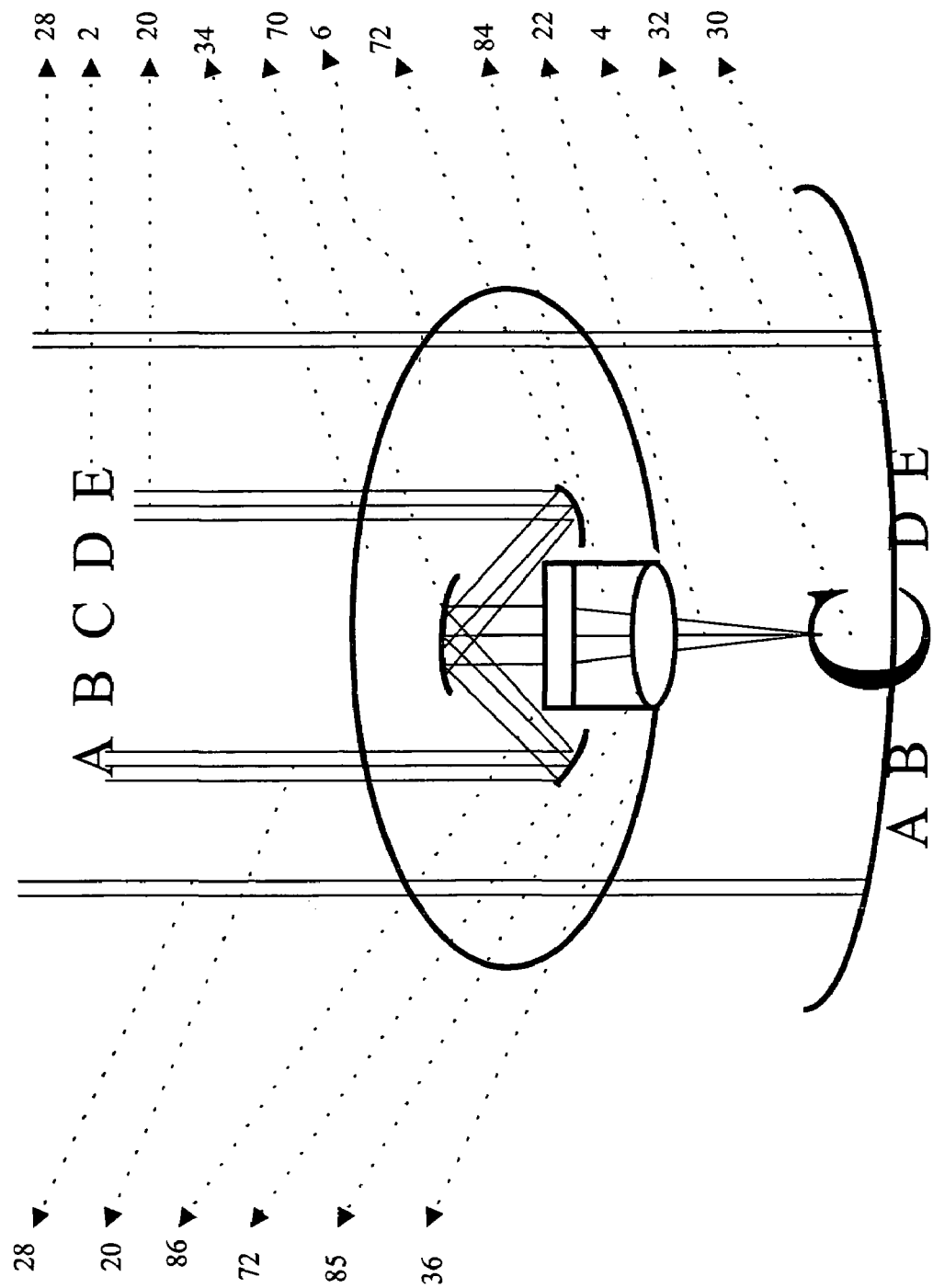
FIG. 17 is a view of the intraocular implant of FIG. 1a having an internally posteriorly mounted central lens arrangement with a plurality of mirrors.

Reference is now made to FIG. 17, which is a view of intraocular implant 6 of FIG. 1*a* having an internally posteriorly mounted central lens arrangement 84 with a plurality of mirrors 70, 72 forming a two-mirror Cassegrain telescope. Arrangement 84 includes lenses 85, 86. Optical element 82 is placed inside lens 10 and the posterior surface of optical element 82 is flush with posterior surface 36 of lens 10.

Figure 18:
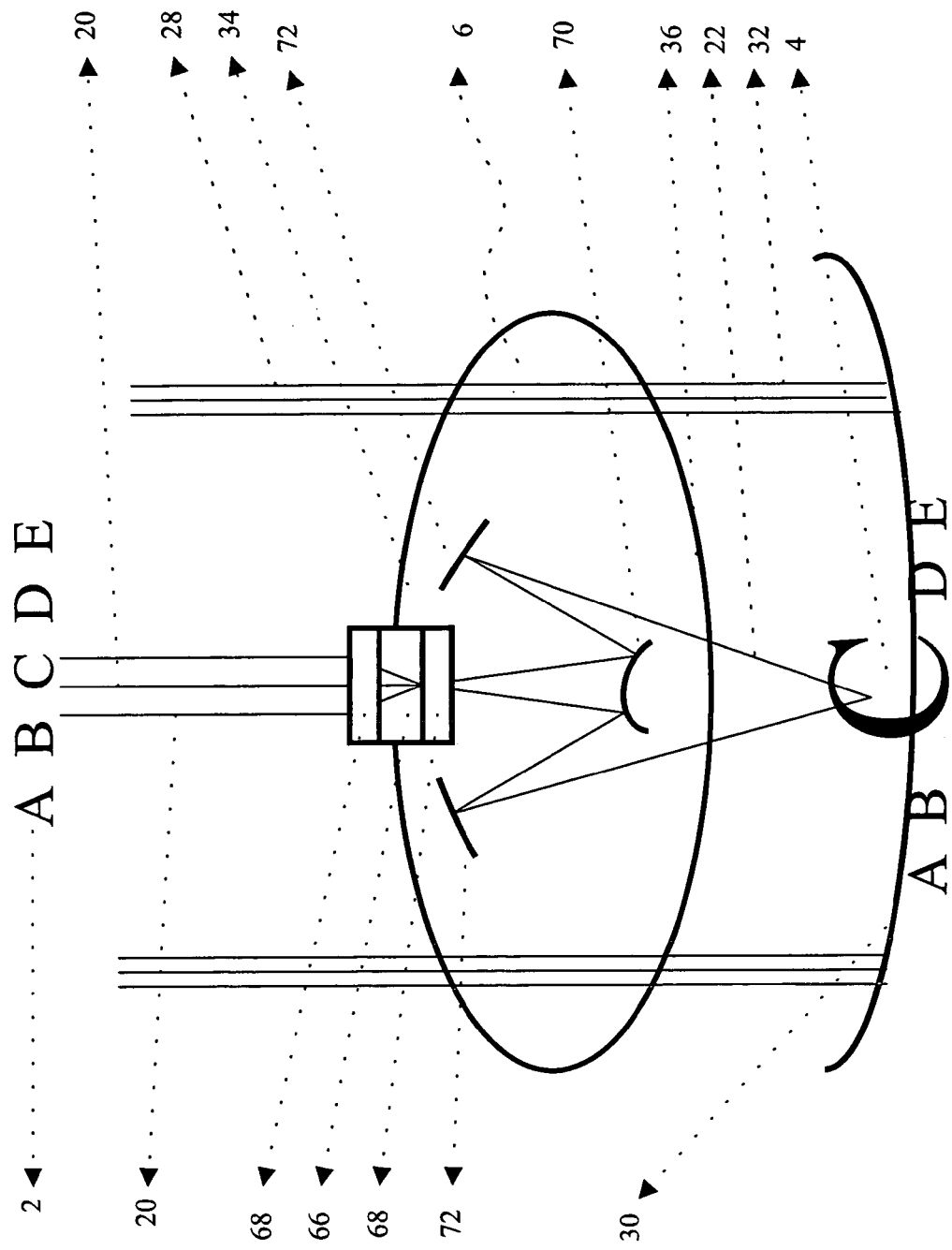
FIG. 18 is a view of the intraocular implant of FIG. 1a having a partially internally anteriorly mounted central lens arrangement with a plurality of mirrors.

Reference is now made to FIG. 18, which is a view of intraocular implant 6 of FIG. 1*a* having a partially internally anteriorly mounted central lens arrangement 66 with a plurality of mirrors 70, 72. Optical element 66 includes lenses 68.

Figure 19:
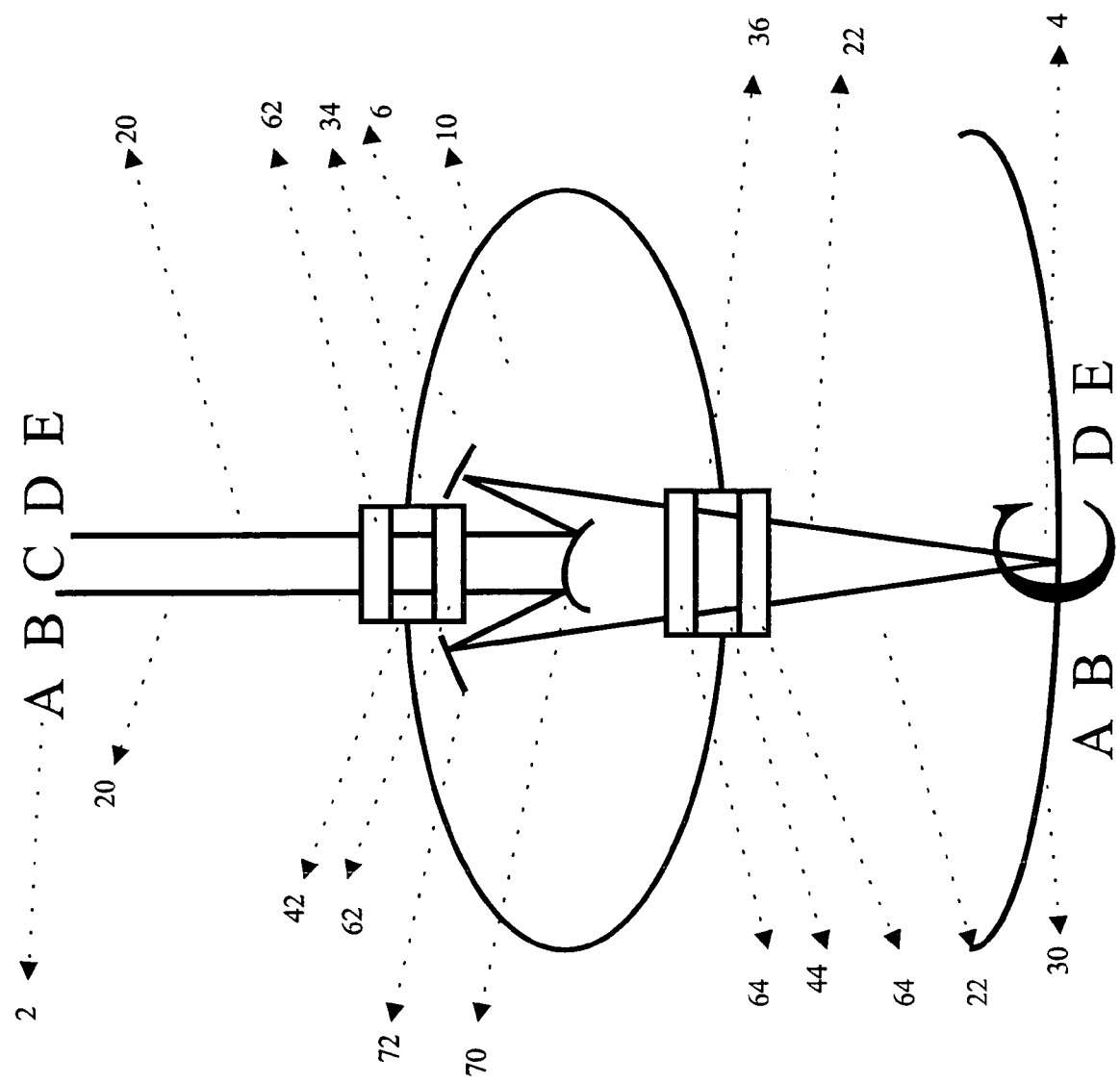
FIG. 19 is a view of the intraocular implant of FIG. 1a having partially internally anteriorly and posteriorly mounted central lens arrangements with a plurality of mirrors.

Reference is now made to FIG. 19, which is a view of intraocular implant 6 of FIG. 1*a* having partially internally anteriorly and posteriorly mounted central lens arrangements 42, 44 with a plurality of mirrors 70, 72 forming a Cassegrain mirror system. Optical elements 42 and 44 include lenses 62 and 64, respectively.

Figure 20:
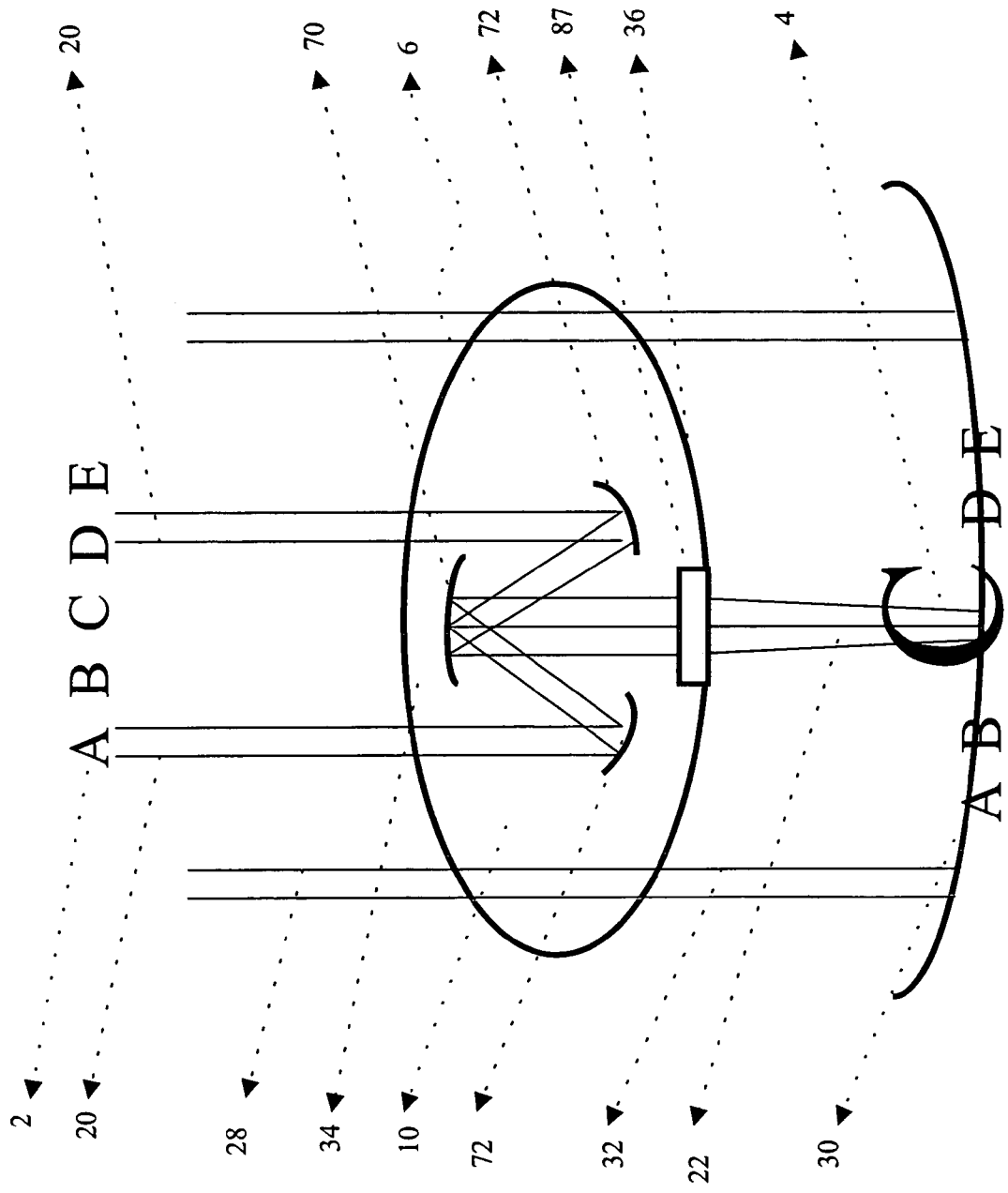
FIG. 20 is a view of the intraocular implant of FIG. 1a having a posteriorly mounted lens with a plurality of mirrors.

Reference is now made to FIG. 20, which is a view of intraocular implant 6 of FIG. 1*a* having a posteriorly mounted lens 87 with a plurality of mirrors 70, 72 forming a Cassegrain type mirror arrangement. It will be appreciated by those ordinarily skilled in the art that single lens 87 can also be disposed anteriorly of lens 10. It will be appreciated by those ordinarily skilled in the art that lens 87 can be externally attached to the posterior or anterior surfaces of lens 10.

Reference is now made to FIGS. 21*a* and 21*b*. FIG. 21*a* is plan view of intraocular implant 6 of FIG. 1*a* having a plurality of internally mounted lens arrangements 92, 93, 94 and a plurality of mirrors 88, 89, 90, 91. FIG. 21*b* is front view of intraocular implant 6 of FIG. 21*a*. It will be appreciated by those ordinarily skilled in the art that optical elements can also be placed: (i) anteriorly of lens 10 so that light passes through the optical element before reaching the first mirror 88, (ii) posteriorly so that light passes through the optical element after it leaves the last mirror 91, or (iii) both anteriorly and posteriorly. It will be appreciated by those ordinarily skilled in the art that mirrors 88, 89, 90, and 91 can be convex or concave, rounded or pointed and therefore take various shapes including spherical and aspheric shapes. It will be appreciated by those ordinarily skilled in the art that optical elements 92, 93 and 94 can contain at least one lens and/or at least one mirror. Additionally, optical elements 92, 93 and 94 can be placed all together or any combination of two of the three lenses or any one of them could be placed individually. Optical elements 92, 93 and 94 can be identical or different from each other. The path of the peripheral light is not shown in FIG. 21. Nevertheless, the peripheral light passes through implant 6 between optical elements 92, 93 and 94 or mirrors 88, 89, 90, and 91.

FIGS. 22*a*–22*d* are views of alternate embodiments of intraocular implant 6 of FIG. 1*a* having at least one internally mounted lens arrangement 92, 93 and a plurality of mirrors 70, 72 forming a Cassegrain mirror system. It will be appreciated by those ordinarily skilled in the art that optical elements 92, 93 can be placed anteriorly or posteriorly, anteriorly and posteriorly, in or external to the light path between mirrors 70, 72. Optical elements 92, 93 typically include one or more lenses and optionally, one or more mirrors. The peripheral light path is not shown in FIG. 22. Nevertheless, the peripheral light passes through implant 6 between optical elements 92, 93 and mirrors 70, 72 reaching the retina after passing through implant 6.

Figure 23:
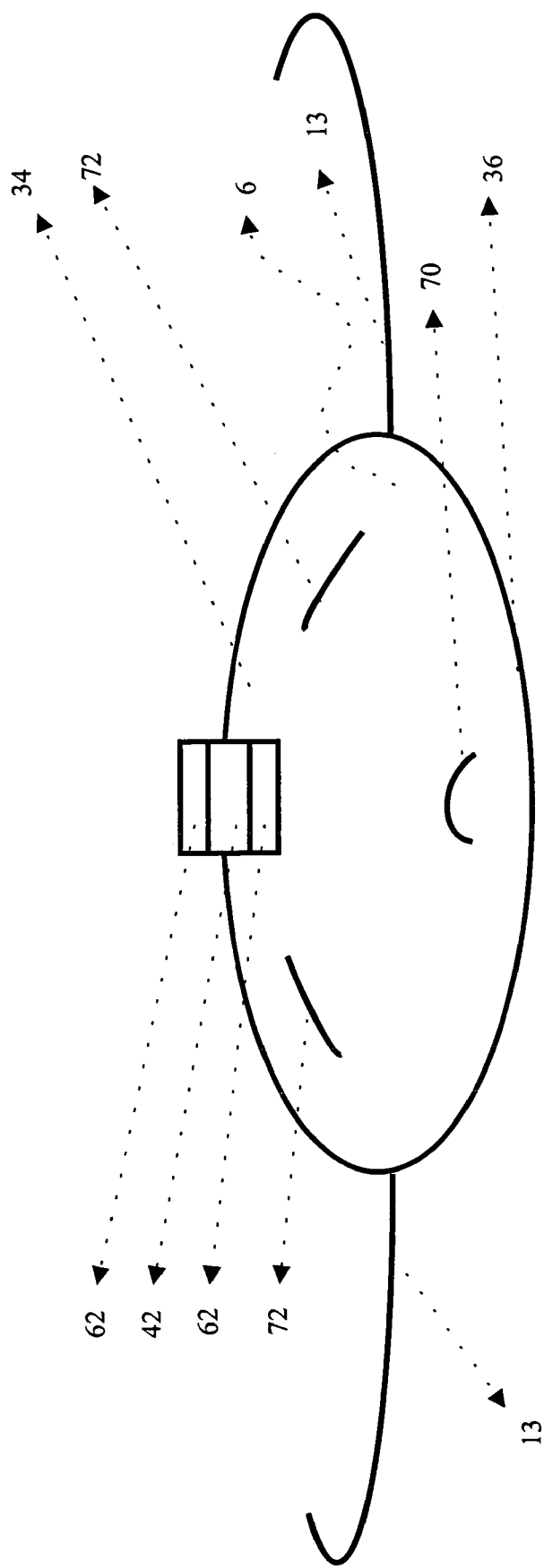
FIG. 23 is a view of the intraocular implant of FIG. 1a having loops for implantation into the eye.

Reference is now made to FIG. 23, which is a view of intraocular implant 6 of FIG. 1*a* having loops 13 for implantation into the eye; This figure illustrates the method of fixation of an IOL, such as implant 6, or any other IOL that is implanted, inside the eye. The use of loops for fixing an IOL into the eye is known to those skilled in the art. This method of implantation can be used for all the embodiments described in this invention. This method of implantation is described here as a background to the novel implantation method described below with reference to FIGS. 24 to 27, 30. Loops 13 serve for fixing implant 6 inside the eye by exerting pressure on the periphery of the capsular bag. It will be appreciated by those ordinarily skilled in the art that all embodiments of implant 6 of the present invention can include at least one loop for fixing implant 6 into the eye.

Figure 24:
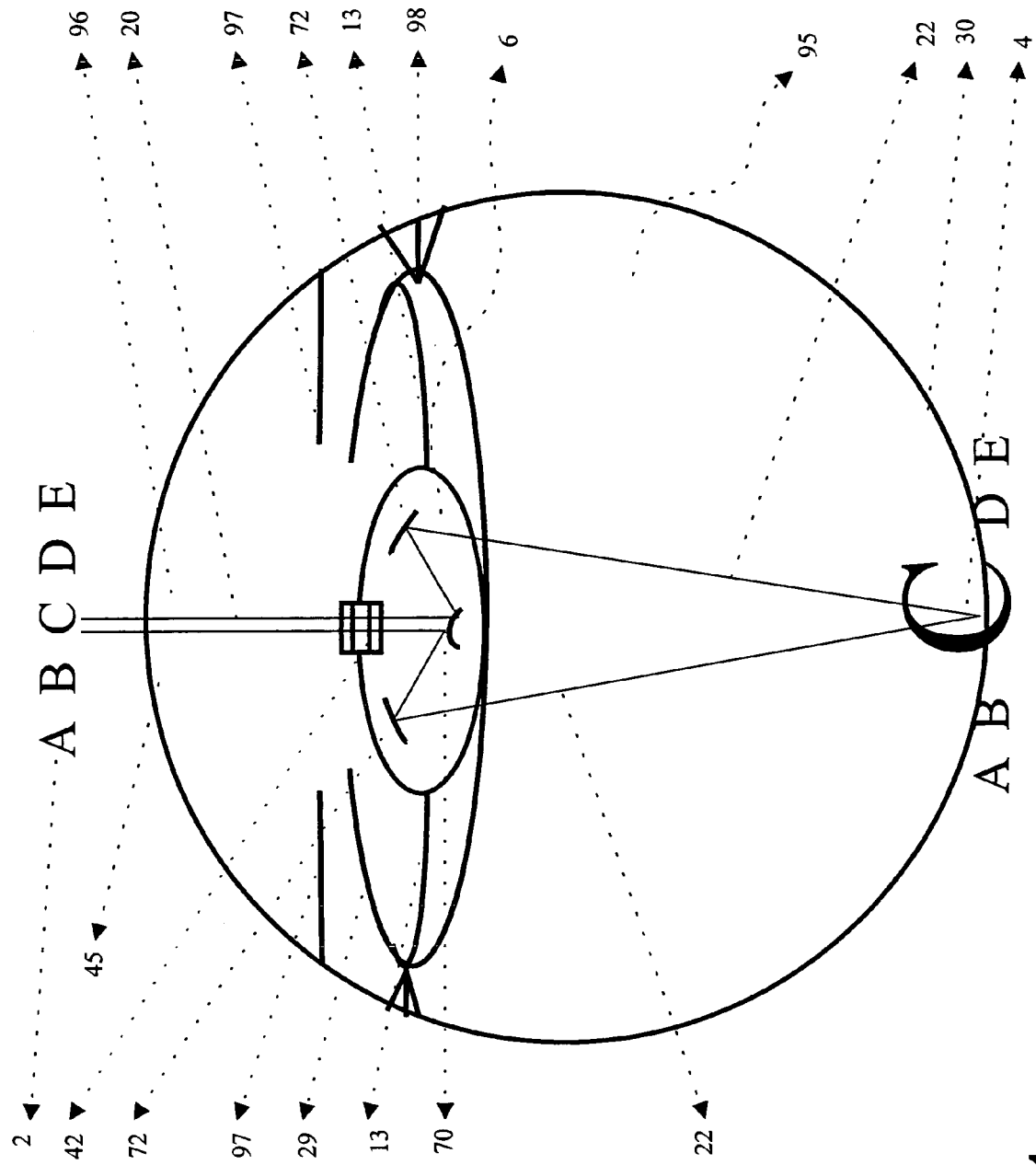
FIG. 24 is a view of a horizontal section of the human eye having the intraocular implant of FIG. 1a implanted therein.

Reference is now made to FIG. 24, which is a view of a horizontal section of a human eye 95 having intraocular implant 6 of FIG. 1*a* implanted therein. Human eye 95 includes a cornea 96, an iris 97 which creates the papillary opening, a zonula 98, a vitreous, and retina 30. Lens capsule 29 contains implant 6. In this figure, implant 6 is implanted so as to replace the natural lens of the eye. Loops 13 are located inside lens capsule 29. Loops 13 exert pressure towards the periphery of capsule 29, similar to a regular IOL, thus stabilizing implant 6 in its position, facing object 2. In operation, the light travels from object 2 through cornea 45 to element 42 and from there to mirrors 70 and 72 and to retina 30. It will be appreciated by those ordinarily skilled in the art that implant 6 can be implanted using other IOL implantation methods known in the art, for example, but not limited to scleral fixation, sulcus fixation and anterior chamber fixation.

Figure 25:
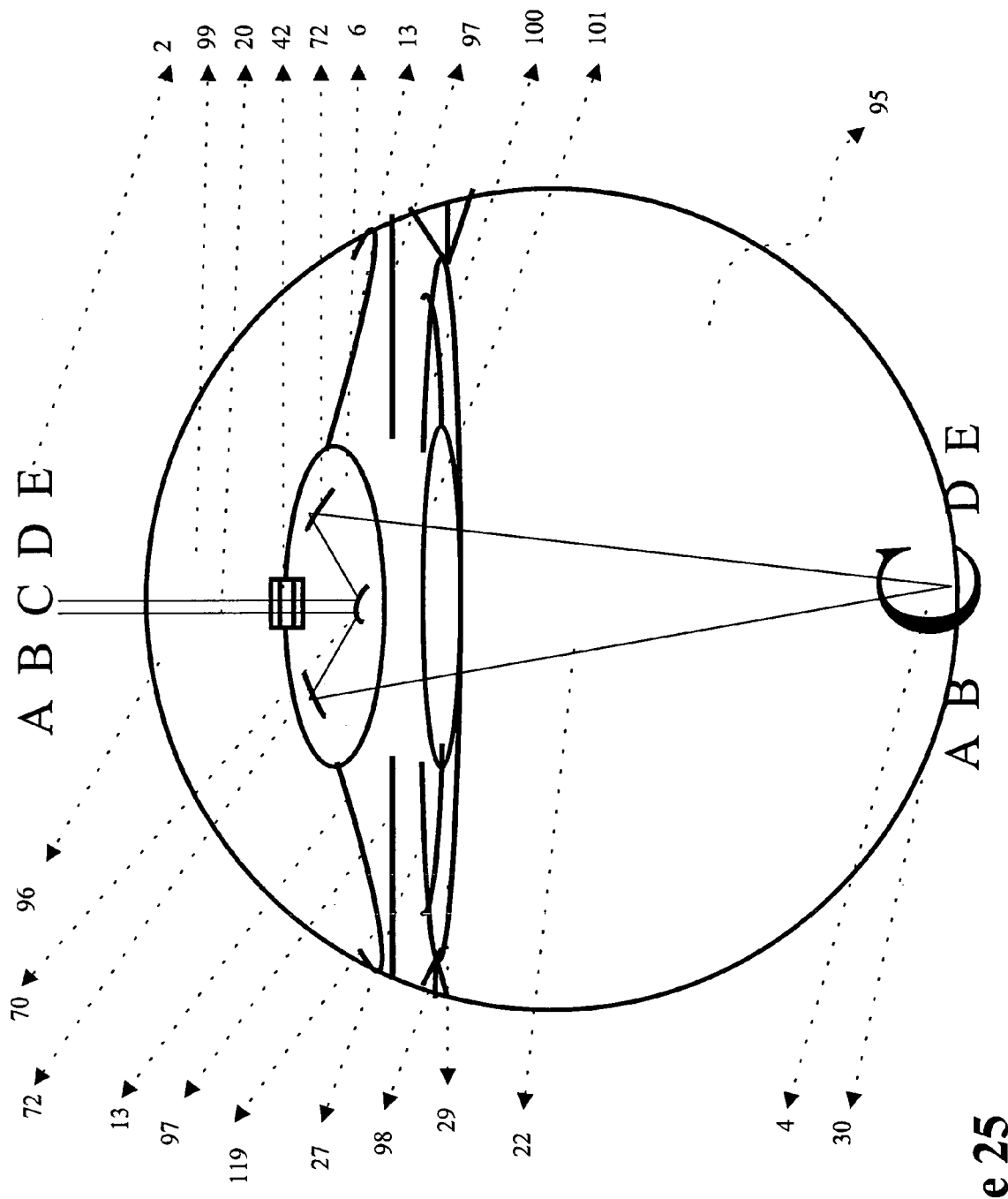
FIG. 25 is a view of horizontal section of a aphakic eye having the intraocular implant of FIG. 1a implanted into the anterior chamber of the eye.
Figure 26:
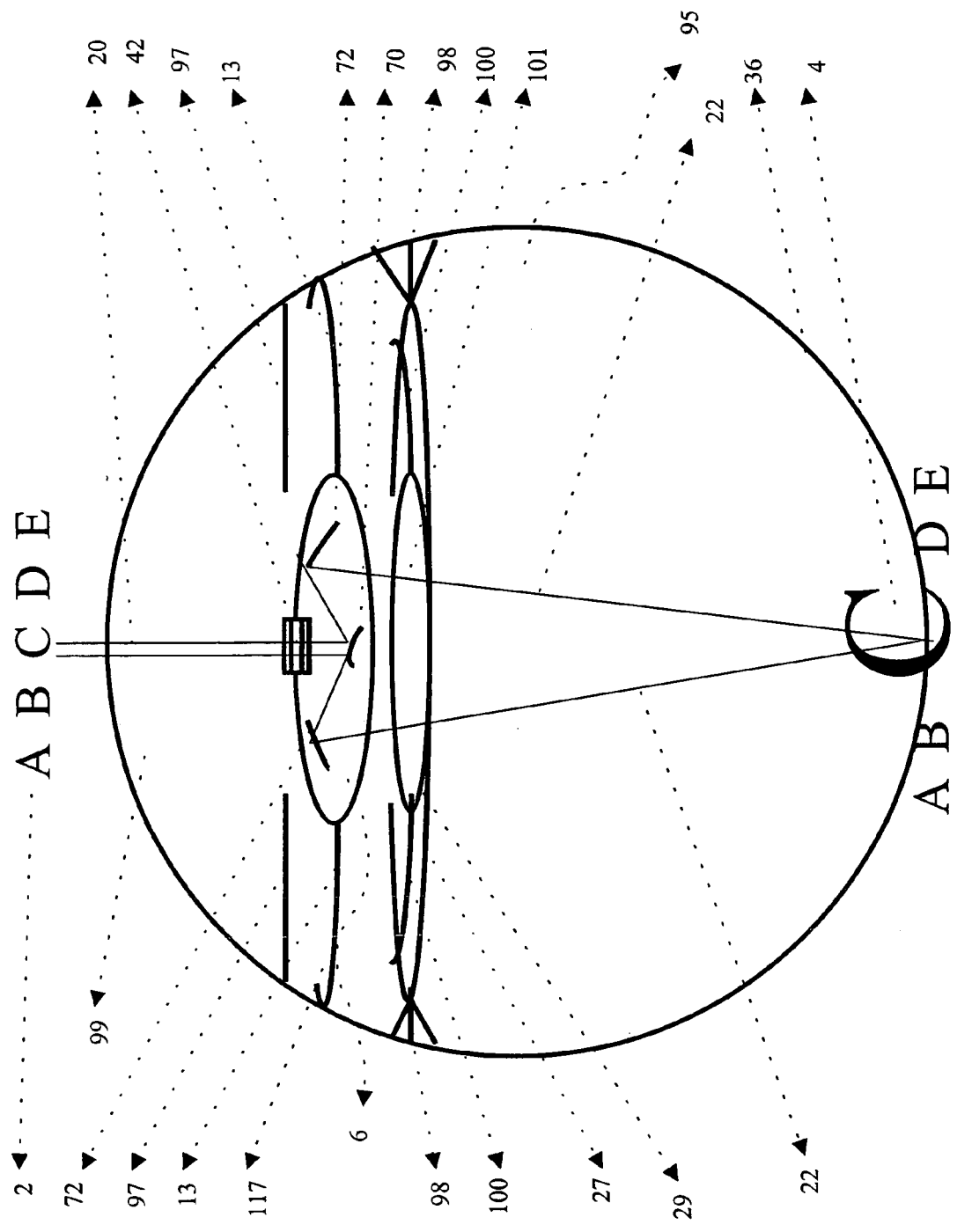
FIG. 26 is a view of horizontal section of a aphakic eye having the intraocular implant of FIG. 1a implanted into the sulcus.
Figure 27:
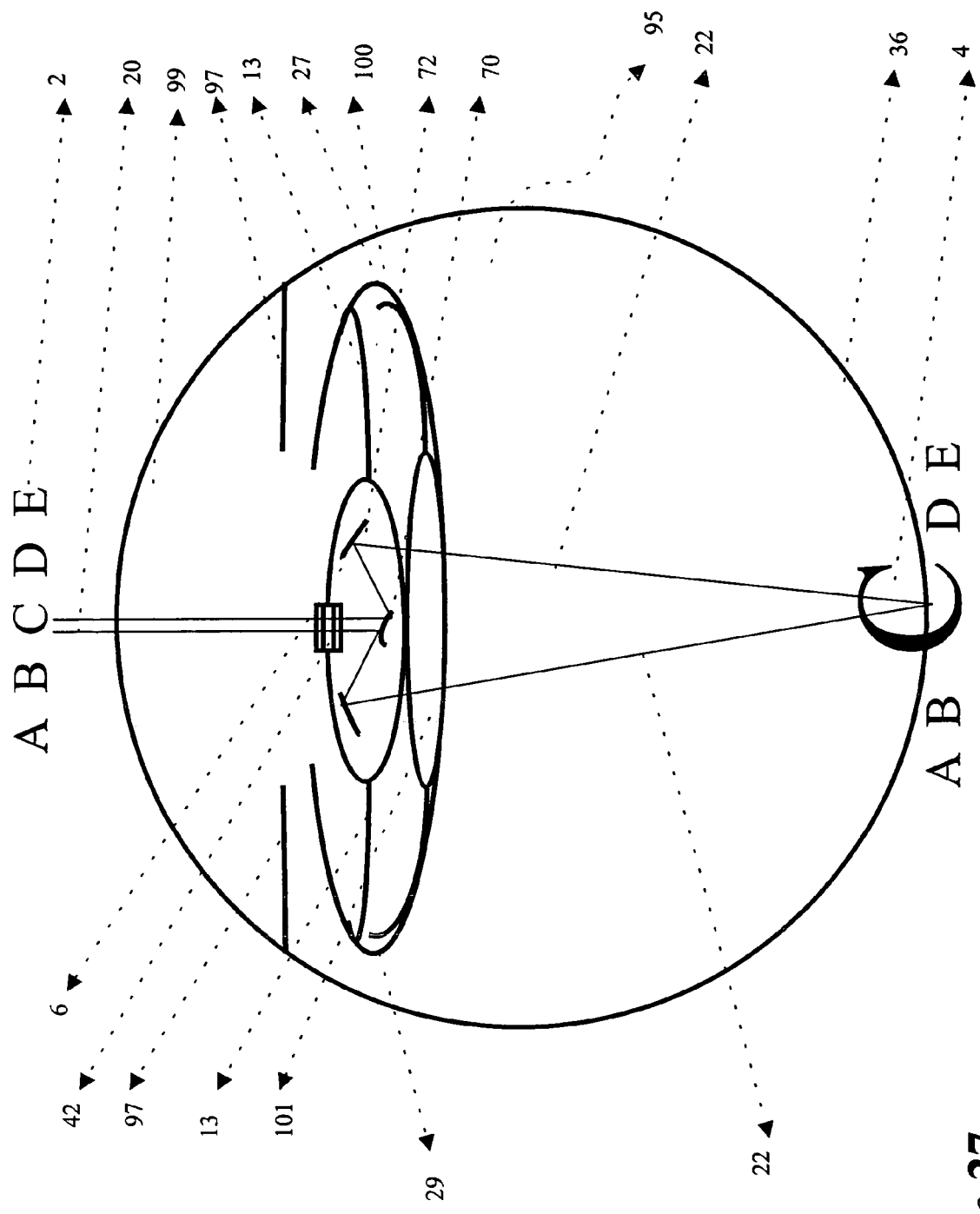
FIG. 27 is a view of horizontal section of a aphakic eye having the intraocular implant of FIG. 1a implanted into the capsular bag.

Reference is now made to FIGS. 25 to 27. FIG. 25 is a view of horizontal section of an aphakic eye 95 having an intraocular implant 101 and implant 6 of FIG. 1*a* implanted into the anterior chamber 99 of eye 95. FIG. 26 is a view of horizontal section of an aphakic eye 95 having intraocular implant 101 and also implant 6 of FIG. 1*a* implanted into the sulcus 117. FIG. 27 is a view of horizontal section of an aphakic eye 95 having intraocular implant 101 and implant 6 of FIG. 1*a* implanted into the capsular bag 29. Implant 6 is configured, such that it can be implanted in eye 95, which has already undergone cataract surgery (aphakic eye). The natural lens of eye 95 was removed and bag 29 was emptied during cataract surgery. A regular intraocular lens implant 101 has previously been implanted into capsular bag 29 using at least one loop 100. In FIG. 25 implant 6 is implanted in anterior chamber 99 of eye 95. Loops 13 for fixation are also located at the anterior chamber angle 119. In FIG. 26, loops 13 are located in the posterior chamber of eye 95, the sulcus 117 as a "piggy-back implant", after implantation of a regular IOL in bag 29 so that loops 13 are located at an angle 117 between iris 97 and ciliary bodyand not in capsular bag 29. In FIG. 27, implant 6 was subsequently implanted into capsular bag 29 using at least one loop as a "piggy back implant". In FIGS. 25 to 27, implant 6 is a secondary implant, for example, but not limited to helping retinal patients improve their vision after having gone through cataract surgery. The optical performance of implant 6 is calculated to take into account the dioptric power of, already implanted, implant 101.

Figure 28:
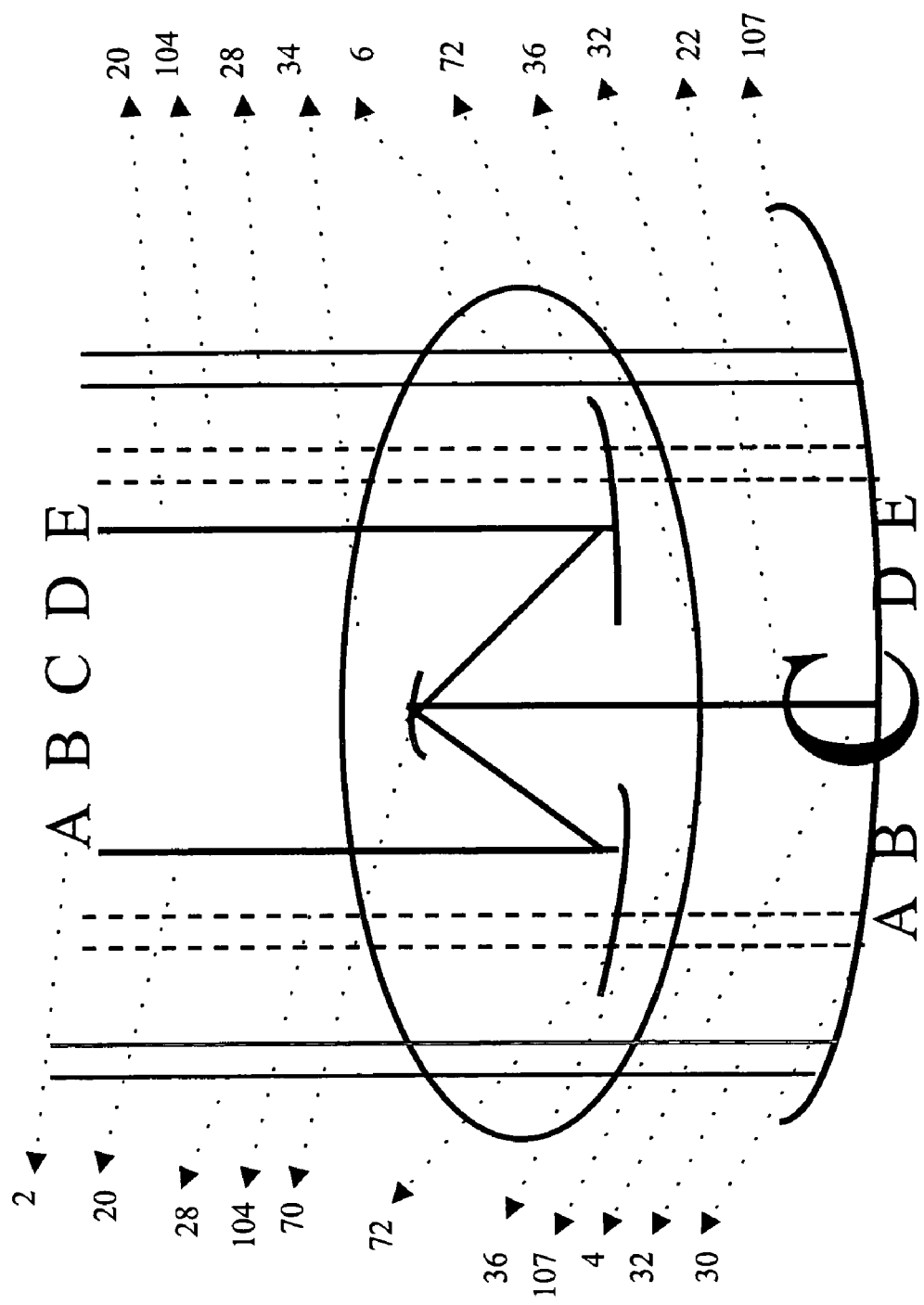
FIG. 28 is a view of the intraocular implant of FIG. 1a having a plurality of mirrors, at least one of which being partially reflecting/partially transmitting.

Reference is now made to FIG. 28, which is a view of intraocular implant 6 of FIG. 1*a* having a plurality of mirrors 70, 72. Mirror 72 has a non-transmitting part for reflecting central light 22 toward mirror 70. Mirror 72 has a partially transmitting section for allowing part of peripheral light 104 to be transmitted to retina 30, as light 107, thereby forming part of the peripheral visual field image. Mirror 70 is a non-transmitting mirror. However, it will be appreciated by those ordinarily skilled in the art that mirror 70 can also be a partially transmitting mirror. It will also be appreciated by those ordinarily skilled in the art that one of the major surfaces of mirror 70 can be non-transmitting and the other major surface of mirror 70 can be transmitting. It will be appreciated by those ordinarily skilled in the art that mirrors 70, 72 can be non-transmitting or transmitting for certain or all frequencies of light. In operation, central light 20 enters implant 6 and is partly reflected by mirror 72 to central mirror 70. Central light 20 is reflected from mirror 70, as light 22, towards retina 30, thereby creating image 4. Peripheral light 28 passes through implant 6 without meeting any mirror on the way and emerges as light 32 travelling towards retina 30. Light 104 reaches mirror 72. Part of light 104 passes through mirror 72, since it is refracted and not reflected by that part of mirror 72. Light 104 emerges from implant 6 as light 107 travelling towards retina 30. It will be appreciated by those ordinarily skilled in the art that the level of reflection of mirrors 70, 72 may vary from point to point on the same mirror. Furthermore, it will be appreciated by those ordinarily skilled in the art that the level of reflection may be different between the various mirrors in the same implant. For example, mirror 72 may reflect certain waves, which mirror 70 does not reflect or part of the mirror 72 (or 70) can be more or less reflective. It will be appreciated by those ordinarily skilled in the art that mirrors 70, 72 can be convex or concave, rounded or pointed and therefore take various shapes including spherical and aspheric shapes.

Figure 29:
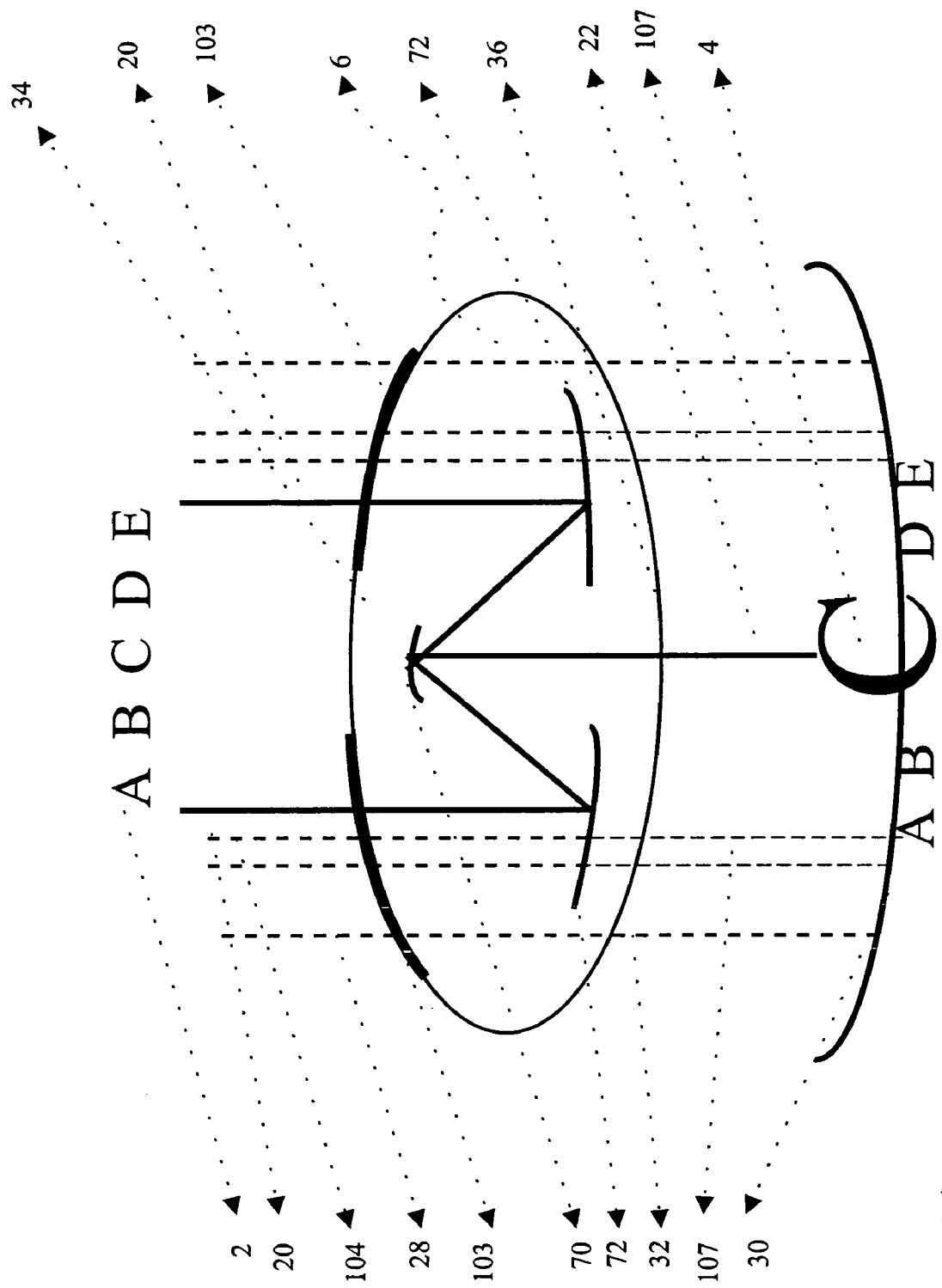
FIG. 29 is a view of the intraocular implant of FIG. 1a having a plurality of mirrors, at least one of which being partially reflecting/partially transmitting disposed on the surface of the main body member lens.

Reference is now made to FIG. 29, which is a view of intraocular implant 6 of FIG. 1*a* having a plurality of mirrors 70, 72, 103. This embodiment is the same as the implant described with reference to FIG. 28 with the addition of mirror 103. An annular portion of the exterior anterior surface of implant 6 is coated with mirror 103 for example, but not limited to adjusting the relative light intensity between the central and peripheral fields. It will be appreciated by those ordinarily skilled in the art that mirror 103 can be located on anterior surface 34 or posterior surface 36 or inside lens 10, mirror 103 can also be non-transmitting, partially or fully transmitting of all or only some frequencies of light. It will also be appreciated by those ordinarily skilled in the art that the level of reflection of mirror 103 may vary from point to point on thereon. Furthermore, the level of reflection may be different between mirrors in the same implant. For example, mirror 72 may reflect certain waves, which mirror 103 does not reflect. Additionally, mirror 103 can be convex or concave, rounded or pointed and therefore take various shapes, including spherical and aspheric shapes. Incoming light is divided to three categories: (i) Central light 20 which emerges from implant 6 as light 22; (ii) peripheral light 28 which emerges from implant 6 as light 32, and (iii) light 104 which is partially reflected and partially refracted by mirror 72 and emerges as light 107.

Figure 30:
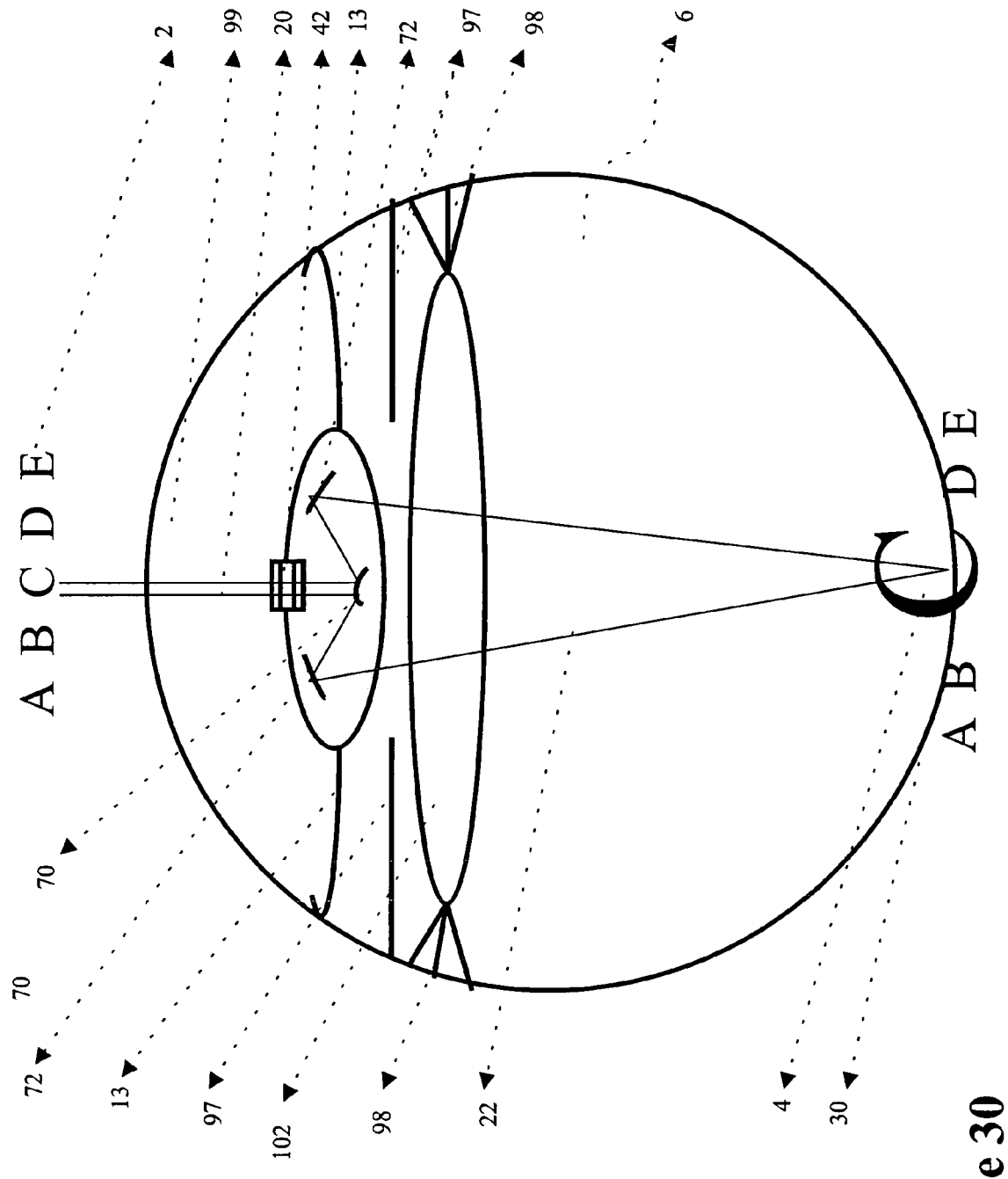
FIG. 30 is a view of horizontal section of a phakic eye having the intraocular implant of FIG. 1a implanted into the anterior chamber of the eye.

Reference is now made to FIG. 30, which is a view of horizontal section of a phakic eye 95 (eye 95 has not undergone a cataract surgery, eye 95 still containing the original crystalline lens 102) having intraocular implant 6 of FIG. 1*a* implanted into the anterior chamber 99 of eye 95. Implant 6 is located in anterior chamber 99 of eye 95 using one or more loops 13 in order to fixate it.

Reference is now made to FIG. 31, which is a view of intraocular implant 6 of FIG. 1*a* having a plurality of reflective coated lenses 105, 106 disposed in implant 6. Lenses 105, 106 form a Cassegrain type mirror telescope. It will be appreciated by those ordinarily skilled in the art that some of the optical elements can be mirrors without lenses or non-coated lenses. It will be appreciated by those ordinarily skilled in the art that lenses 105, 106 can be coated anteriorly, posteriorly or interiorly disposed, as described with reference to FIGS. 32a to 32g. Additionally, It will be appreciated by those ordinarily skilled in the art that the mirrors may cover part or the entire lens and may have more than two different levels of reflection for the same mirror. Also, lens 105 and lens 106 can have the same or different levels of reflection and refractive indices. Lenses 105, 106 are for example, but not limited to, convex, concave, plano, spherical, aspheric, irregular, asymmetric, astigmatic, prismatic, holographic or graded index configuration, or some combination thereof. In operation, central light 20 enters implant 6 and passes through lens 106 where light 20 is reflected, partly or fully towards central mirror 105. Central light 20 is then reflected partially or fully towards retina 30. Peripheral light 28 enters implant 6 and emerges as light 32.

FIGS. 32a to 32g are views of coated lenses for use with implant 6 of FIG. 31. These figures show concave and convex lenses 160. The lenses are coated by a reflective material 162 either externally (anteriorly and/or posteriorly) or internally. In the embodiments shown in FIGS. 32e to 32g reflecting surface 162 has a more reflecting portion 164 and a less reflecting portion 166. It should be noted that the refraction and reflection levels of lenses 160 and surfaces 162 depend on the combination of the refraction and reflection of the lenses and the refraction and reflection of the mirrors 162 that are attached to lenses 160.

Figure 33:
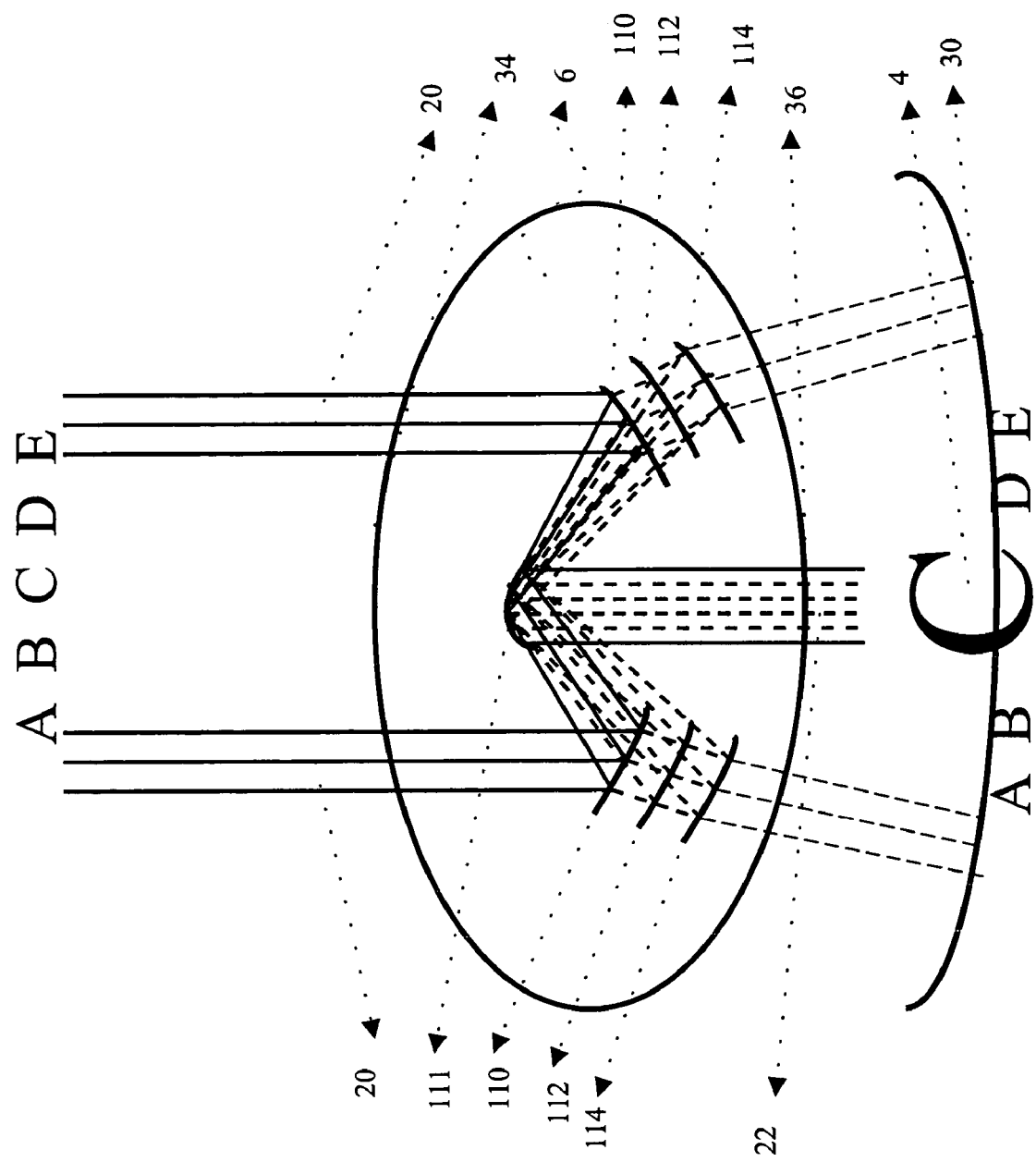
FIG. 33 is a view of the intraocular implant of FIG. 1a having a plurality of partially reflecting/partially transmitting mirrors arranged in succession.

Reference is now made to FIG. 33, which is a view of intraocular implant 6 of FIG. 1a having a plurality of partially reflecting/partially transmitting mirrors 110, 112, 114 arranged in succession. Mirrors 110, 112, 114 typically have different levels of reflection and refraction of light from each other, as well as reflecting different frequency ranges of light. The advantages of this embodiment includes assisting patients having limitations in depth of focus by providing them with monocular stereopsys. Mirrors 110, 112 and 114 reflect different frequency ranges of light. Central light 20 reaches mirror 110. Mirrors 110, 111, 112, 114 are arranged such that: (i) Part of light 20 is reflected to a central mirror 111 but another part of light 20 is transmitted by mirror 110 and travels to mirror 112; (ii) mirror 112 reflects part of the incident light to mirror 111; (iii) Mirror 112 refracts part of the incident light to mirror 114; (iv) Mirror 114 reflects part of the incident light to mirror 111; (v) Mirror 114 refracts part of the incident light to retina 30; and (vi) Central mirror 111 receives various wavelengths from mirrors 110, 112, 114 and reflects them to retina 30. Mirrors 110, 112 and 114 are annular shaped mirrors. However, it will be appreciated by those ordinarily skilled in the art that mirrors 110, 112, 114 can be non-annular and disposed at various positions within implant 6. Also, mirrors 110, 111, 112, 114 can be convex or concave, rounded or pointed and therefore take various shapes including spherical and aspheric shapes, reflective on one side and/or transparent on the other side. Image 4 projected onto retina 30 is a three-dimensional image if the light that comes from the different mirrors 110, 112, 114 reaches retina 30 as different sinusoidal angles. It will be appreciated by those ordinarily skilled in the art that implant 6 can have more than one central mirror, each central mirror having different levels of reflection instead of, or in addition to, the successive peripheral mirrors described above. Obviously, the mirrors may be of different shapes, different locations, in different numbers, transmit different wavelengths of light, and reflect different wavelengths of light.

Figure 34:
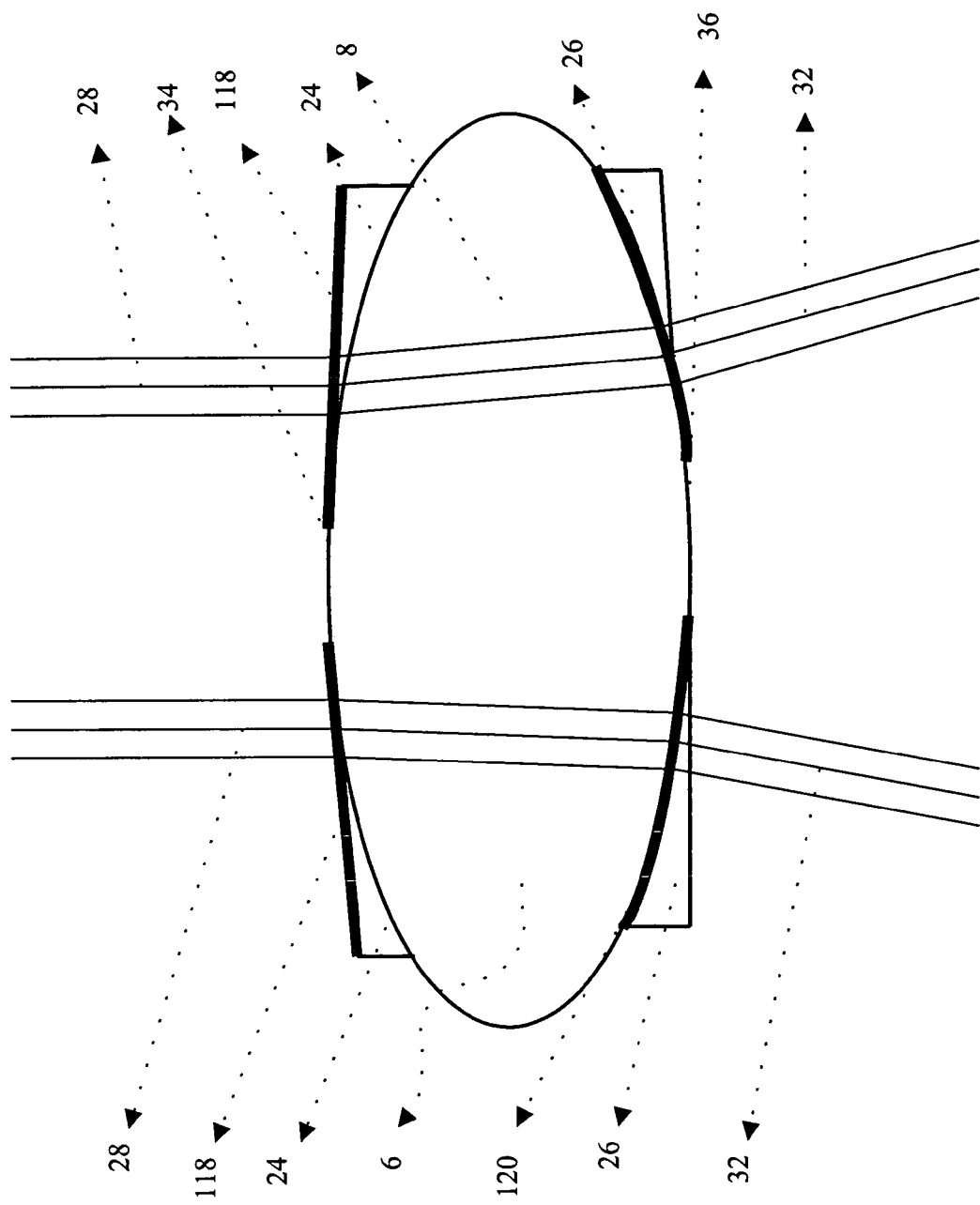
FIG. 34 is a view of the intraocular implant of FIG. 1a configured to form a continuous image on the retina, the implant including at least one partially reflecting/partially transmitting mirror.

Reference is now made to FIG. 34, which is a view of intraocular implant 6 of FIG. 1a configured to form a continuous image on the retina, implant 6 including a plurality of partially reflecting/partially transmitting mirrors 118, 120. This figure does not show central magnifying or minifying optical elements as this figure is brought to explain a novel treatment of the peripheral vision field. However, it will be appreciated by those ordinarily skilled in the art that central vision can be addressed using any of the embodiments described with reference to the attached figures or any other suitable optical arrangement. Implant 6 includes optical elements 24, 26 (described above with reference to FIG. 1a). Elements 24, 26 are coated with mirrors 118, 120, respectively. It will be appreciated by those ordinarily skilled in the art that mirrors 118, 120 can be disposed inside elements 24, 26 or external to any side of elements 24, 26, respectively. It will be appreciated by those ordinarily skilled in the art that mirrors 118, 120 can be convex or concave, rounded or pointed and therefore take various shapes including spherical and aspheric shapes.

Figure 35:
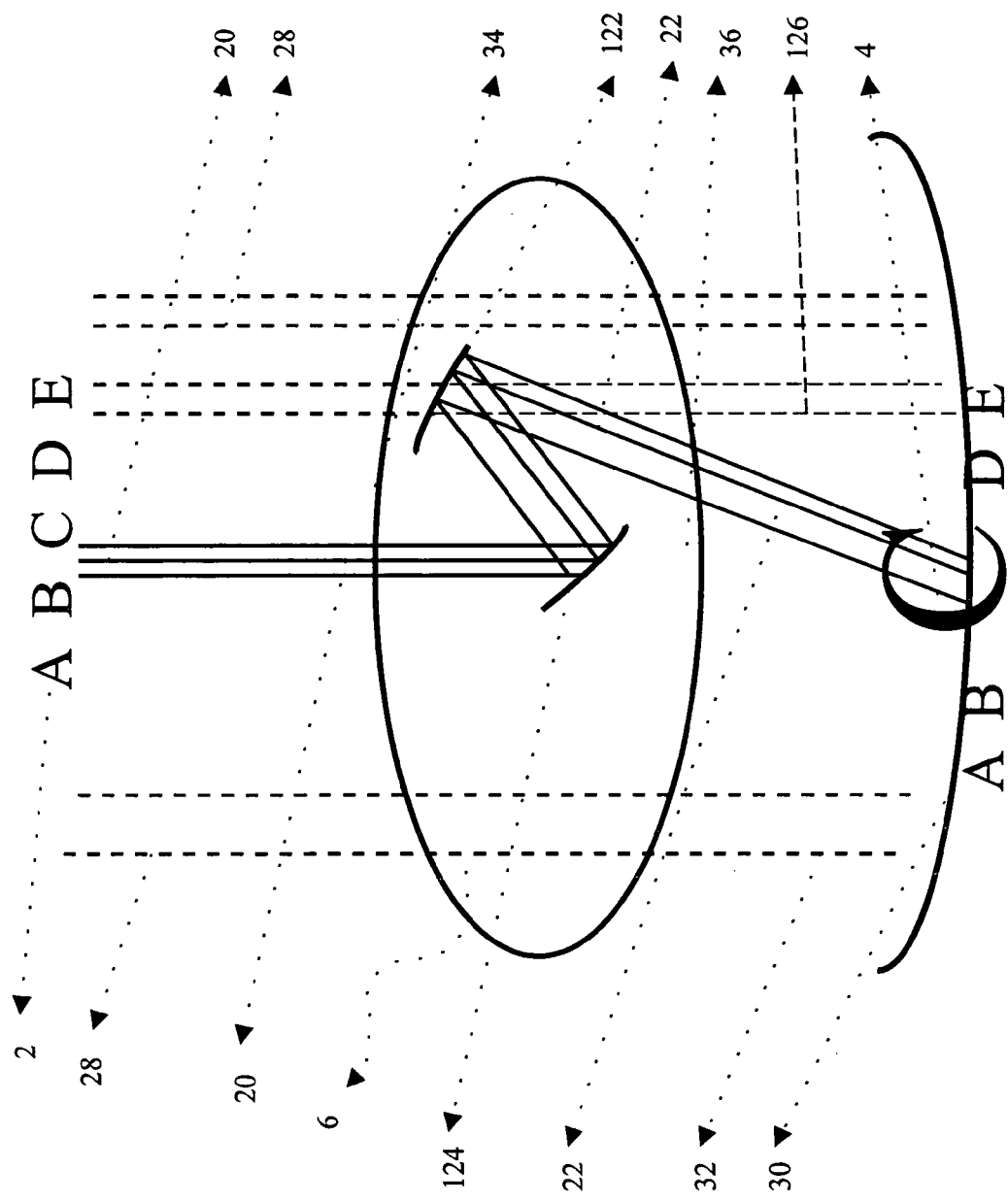
FIG. 35 is a view of the intraocular implant of FIG. 1a including two off axis mirrors, one of the mirrors being partially reflecting/partially transmitting.

Reference is now made to FIG. 35, which is a view of intraocular implant 6 of FIG. 1a including two mirrors 122, 124, mirror 122 being configured for: (i) reflecting light from one of the major surfaces of mirror 122; and (ii) transmitting light from the other major surface of mirror 122. In operation, central light 20 enters implant 6 and is reflected by mirror 124 to mirror 122. Mirror 122 reflects the incident light, as light 22, to retina 30. It will be appreciated by those ordinarily skilled in the art that when mirror 124 is a partially transmitting mirror, some of the light 20 is transmitted by mirror 124 directly to retina 30 and is not reflected by mirror 124 to mirror 122. Peripheral light 28 does not reach any of the mirrors and emerges from implant 6, as light 32, before reaching retina 30. Some of the light entering implant 6 is incident on the anterior surface of mirror 122 and is transmitted by mirror 122 as light 126 to retina 30.

Figure 36:
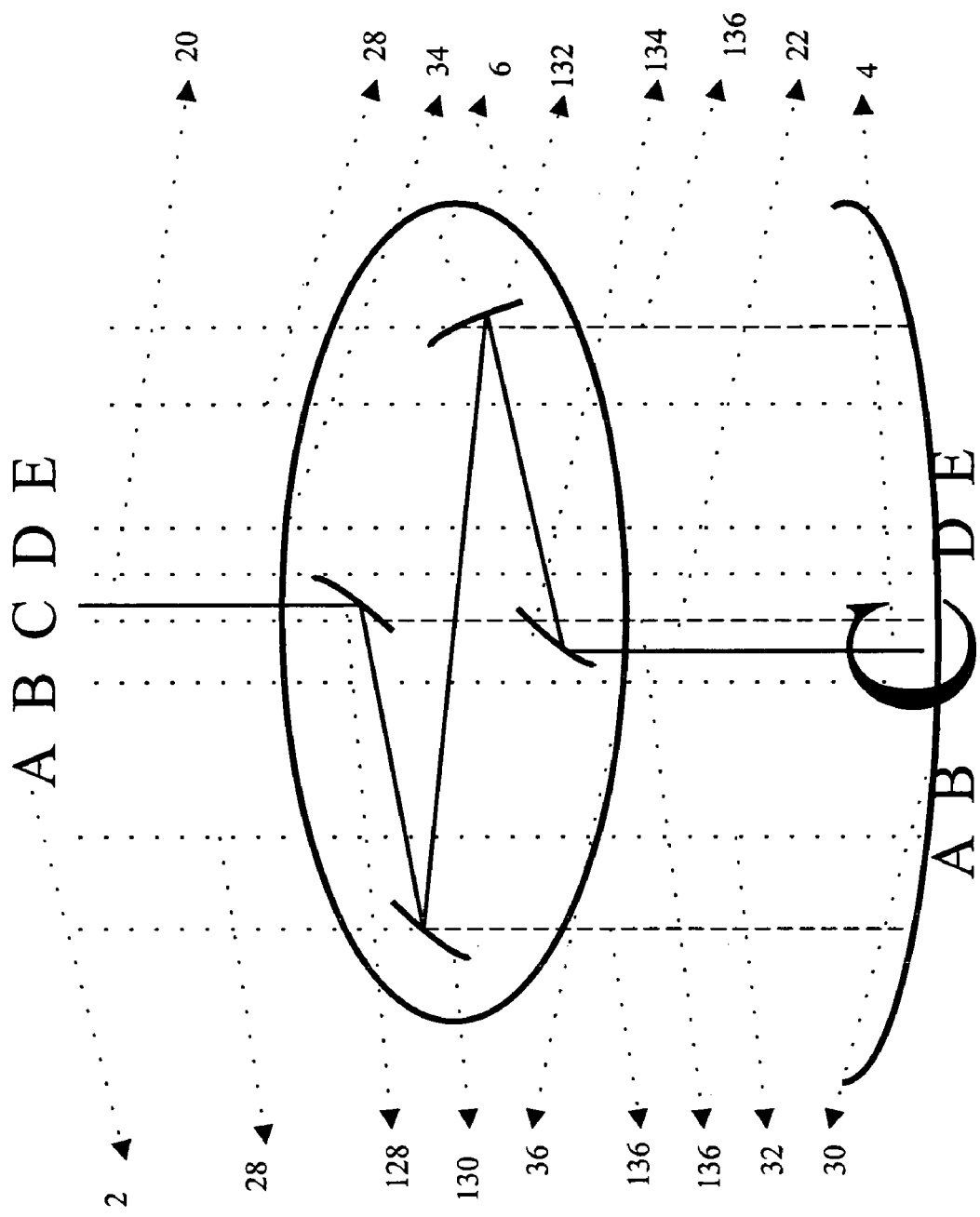
FIG. 36 is a view of the intraocular implant of FIG. 1a having a four-mirror system, the mirrors having various reflecting/transmitting properties.

Reference is now made to FIG. 36, which is a view of intraocular implant 6 of FIG. 1a having a four-mirror system 128, 130, 132, 134. The four-mirror system is configured to create the magnification or minification of the central image. Mirror 128 and 134 are typically configured to partially transmit and partially reflect light incident on the same surface. Mirrors, 130, 132, are configured to fully reflect light from one of their major surfaces and to transmit light incident on the other major surface. It will be appreciated by those ordinarily skilled in the art that the mirrors 128, 130, 132, 134 can be disposed in other arrangements as well as having other reflection and transmission properties. It will be appreciated by those ordinarily skilled in the art that mirrors 128, 130, 132 and 134 can be convex or concave, rounded or pointed and therefore take various shapes including spherical and aspheric shapes. Central light 20 enters implant 6 and reaches mirror 128. From there some of the light is reflected to mirror 130 and some of the light is transmitted to mirror 134. At mirror 134, this transmitted light is further transmitted to retina 30. Mirror 130 reflects light to mirror 132. Mirror 132 reflects this light to mirror 134 which reflects the light to retina 30, forming the central field image. Furthermore, peripheral light 28 is not blocked or reflected by any of mirrors 128, 130, 132, 134. Incident peripheral light 28 emerges from implant 6, as light 32, before reaching retina 30.

Figure 37:
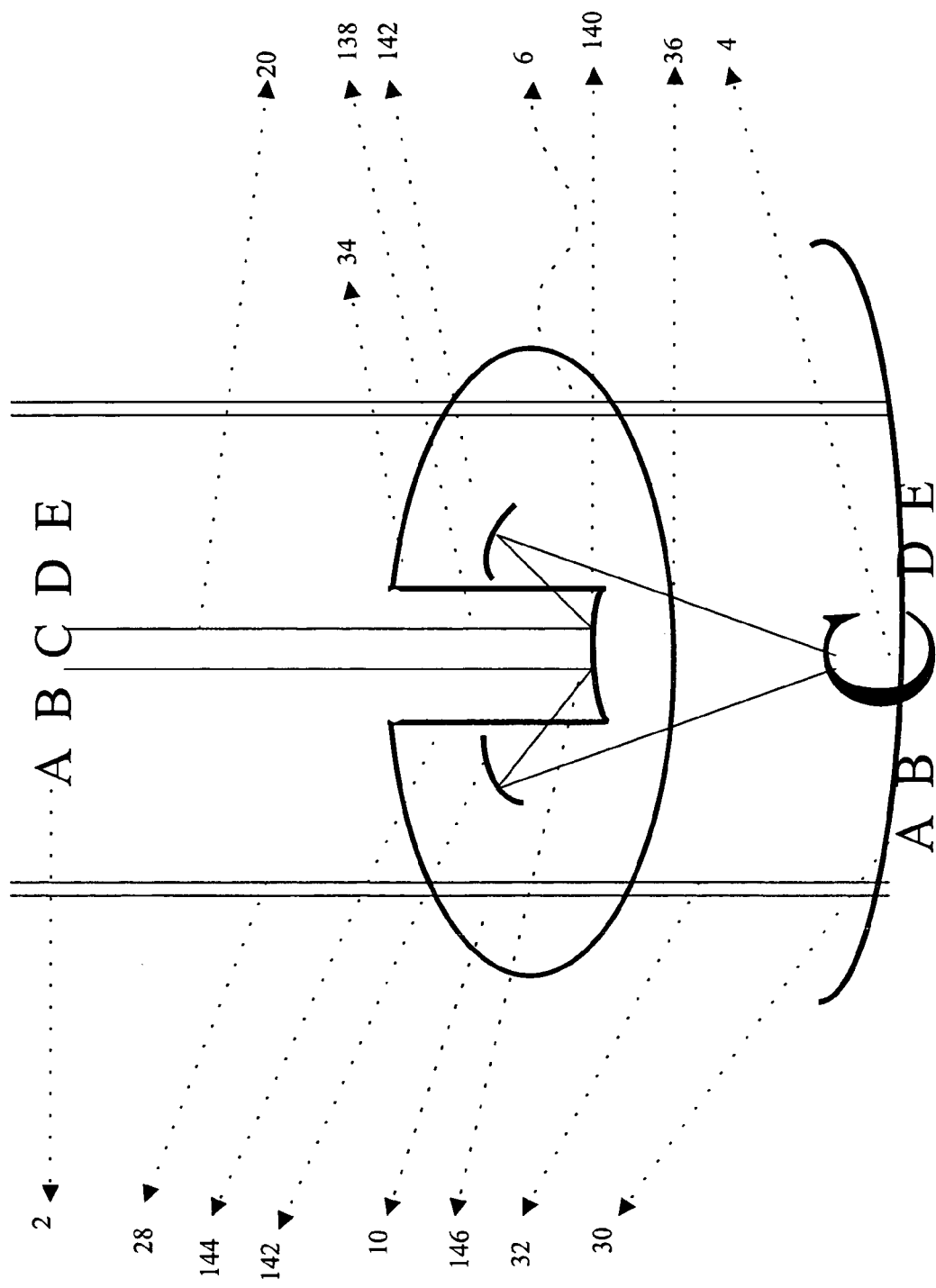

FIG. 37 is a view showing a first method of manufacture of intraocular implant 6 of FIG. 1a. Implant 6 has a non-through-hole 138 formed in lens 10. The base 140 of hole 138 is curved. This curvature has the precise shape needed for forming a central mirror. In operation, entering light reaches the central mirror and is diverted towards mirror 142 and from there to retina 30. It will be appreciated by those ordinarily skilled in the art that hole 138 can be of any shape (rounded or pointed and therefore take various shapes including spherical and aspheric shapes). Base 140 is covered with mirror coating to form the central mirror. After creating the central mirror 140, hole 138 is either, optionally, left open (to be filled with eye fluids), or filled with any material that fills it fully or partially. This filing material may have the same index of refraction as the materials used in lens 10 or a different index of refraction than the material used in lens 10. The optical properties of this filling material may help in diverting the light to predetermined targets such as mirror 142 and/or magnifying or minifying the central image along with the mirrors and other optical elements in implant 6. Furthermore, wall 144 of hole 138 is configured to either enable light to pass through wall 144 in a modified or unmodified state. Optionally, wall 144 is coated with a fully or partially reflective mirror.

Figure 38:
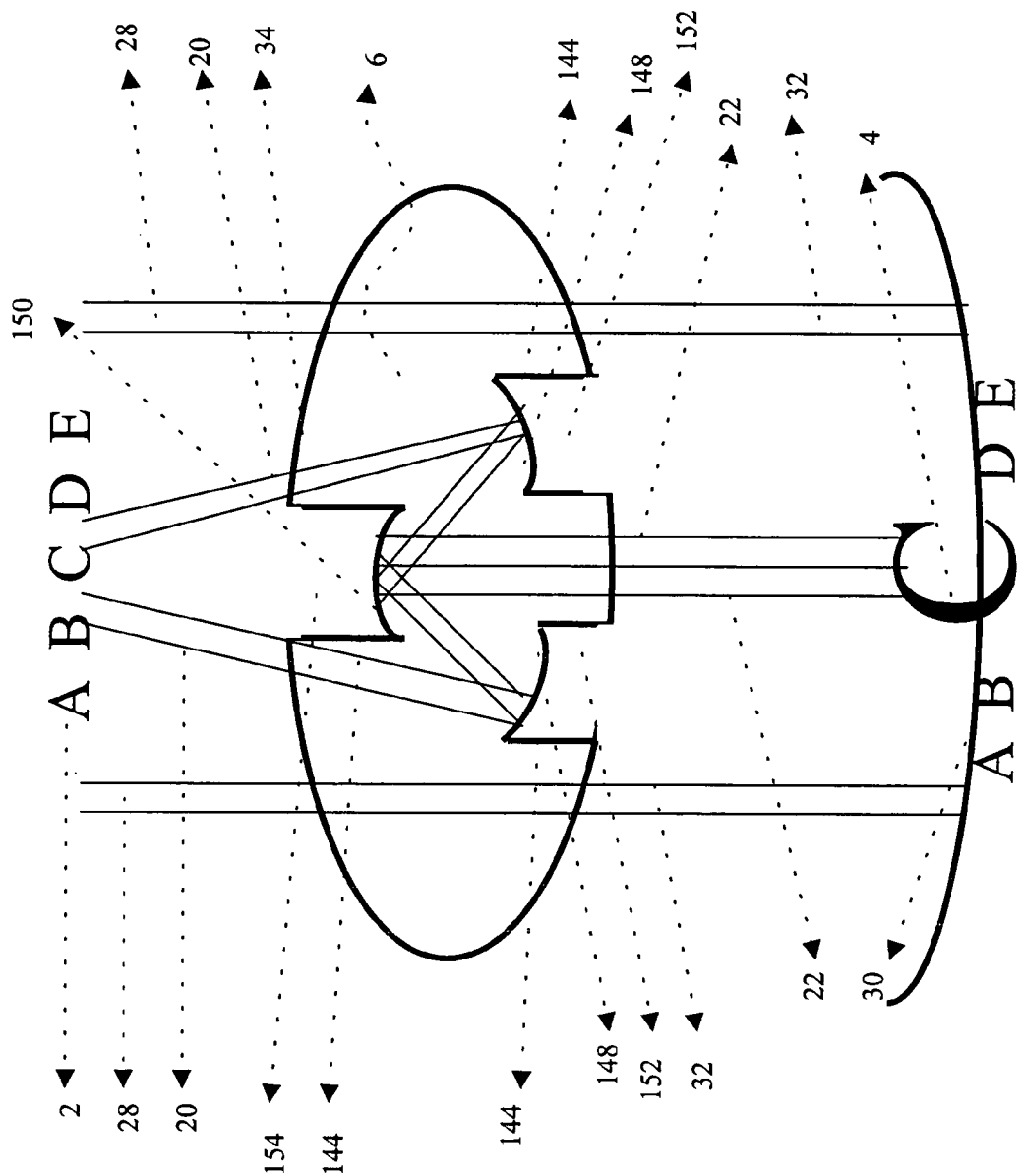

Reference is now made to FIG. 38, which is a view showing a method how to manufacture intraocular implant 6 of FIG. 1a having more than one mirror. Holes 152, 154 are formed in lens 10 to define the curvatures of mirrors 148 and 150.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art which would occur to persons skilled in the art upon reading the foregoing description.

What is claimed is:

1. An intraocular implant for implantation into the interior of a human of a human eye, the eye having a retina, the implant comprising:
    (a) a body member, said body member having an anterior surface and a posterior surface, said body member having optical properties; and
    (b) an optical arrangement configured for forming a first image on the retina, said first image being an image of at least part of the central visual field, at least one of said body member and said optical arrangement being configured for forming a second image on the retina, said second image being an image of at least part of the peripheral visual field.

2. The implant of claim 1, further comprising at least one optical element configured for reducing or preventing, at least one of, overlap and over-spacing, of said first image and said second image on the retina.

3. The implant of claim 1, further comprising at least one optical element configured for adjusting the relative light intensity between said first image and said second image.

4. The implant of claim 1, further comprising:
    (a) at least one optical element configured for reducing or preventing, at least one of, overlap and over-spacing, of said first image and said second image on the retina; and
    (b) at least one optical element configured for adjusting the relative light intensity between said first image and said second image.

5. The implant of claim 1, wherein said optical arrangement includes at least two lenses, said two lenses defining an optical path between said two lenses, said optical arrangement including at least one mirror disposed externally to said optical path.

6. The implant of claim 1, wherein said optical arrangement includes at least two lenses and at least one mirror, said two lenses defining an optical path between said two lenses, said at least one mirror being disposed in said optical path.

7. The implant of claim 1, wherein said optical arrangement is configured such that, at least part of the light forming said second image crosses the path of at least part of the light forming said first image.

8. The implant of claim 1, wherein said optical arrangement is disposed at least partially within said body member.

9. The implant of claim 1, wherein said optical arrangement is completely surrounded by said body member.

10. The implant of claim 1, wherein said optical arrangement includes at least one mirror.

11. The implant of claim 1, wherein said optical arrangement includes a plurality of mirrors, each of said mirrors having a major surface which is configured for partially transmitting and partially reflecting light, said mirrors being arranged such that, light transmitted by one of said mirrors impacts the major surface of another of said mirrors.

12. The implant of claim 11, wherein said mirrors are configured to produce monocular stereopsys.

13. The implant of claim 1, wherein said optical arrangement includes a plurality of lenses.

14. The implant of claim 1, wherein said optical arrangement includes at least one lens and at least one mirror.

15. The implant of claim 1, wherein said optical arrangement includes at least one mirror having a surface which is configured for partially transmitting and partially reflecting light.

16. The implant of claim 1, wherein said optical arrangement includes at least one mirror having a first major surface configured for transmitting light and a second major surface configured for reflecting light.

17. The implant of claim 16, wherein said optical arrangement includes at least one mirror having a surface which is configured for partially transmitting and partially reflecting light.

18. The implant of claim 1, wherein said optical arrangement includes at least one lens, said lens including a reflective material disposed on at least one of, an external surface of said lens and an interior portion of said lens.

19. The implant of claim 1, wherein said body member has an inner portion and an outer portion.

20. The implant of claim 1, wherein said body member is at least partially foldable.

21. A method for improving vision, comprising the steps of:
    (a) providing an implant having a body member and an optical arrangement, said body member having an anterior surface and a posterior surface, said body member having optical properties, said optical arrangement being configured for forming a first image on the retina of an eye, said first image being an image of at least part of the central visual field, at least one of said body member and said optical arrangement being configured for forming a second image on the retina, said second image being an image of at least part of the peripheral visual field; and
    (b) implanting said implant into the eye.

22. The method of claim 21, further comprising the step of implanting a conformer into the eye, wherein said step of implanting said implant is performed by inserting said implant into said conformer.

23. The method of claim 21, wherein said step of implanting is performed while another intraocular lens is implanted in the eye.

24. The method of claim 21, wherein said step of implanting is performed while the natural lens of the eye is still in the eye.

25. The method of claim 21, wherein said step of implanting is performed by implanting said implant in a location in the eye, the location being selected from the group consisting of the capsular bag of the eye, the anterior chamber of the eye, the posterior chamber of the eye and the sulcus.

* * * * *